United States Patent
Yokozeki

(10) Patent No.: US 6,582,374 B2
(45) Date of Patent: Jun. 24, 2003

(54) AUTOMATIC BLOOD-PRESSURE MEASURING APPARATUS

(75) Inventor: Akihiro Yokozeki, Komaki (JP)

(73) Assignee: Colin Corporation, Komaki (JP)

( * ) Notice: Subject to any disclaimer, the term of this patent is extended or adjusted under 35 U.S.C. 154(b) by 0 days.

(21) Appl. No.: 09/977,344

(22) Filed: Oct. 16, 2001

(65) Prior Publication Data

US 2002/0099298 A1 Jul. 25, 2002

(30) Foreign Application Priority Data

Jan. 22, 2001 (JP) ......................... 2001-013097

(51) Int. Cl.⁷ .................................................. A61B 5/02
(52) U.S. Cl. ....................... 600/494; 600/490; 600/485
(58) Field of Search ................................ 600/485–499

(56) References Cited

U.S. PATENT DOCUMENTS

| | | | |
|---|---|---|---|
| 5,255,686 A | * 10/1993 | Takeda et al. | 600/494 |
| 5,279,303 A | 1/1994 | Kawamura et al. | |
| 5,522,395 A | * 6/1996 | Shirasaki et al. | 600/495 |
| 5,682,898 A | * 11/1997 | Aung et al. | 600/484 |
| 5,931,790 A | 8/1999 | Peel, III | |
| 6,036,652 A | * 3/2000 | Inukai et al. | 600/493 |
| 6,491,638 B2 | * 12/2002 | Oka | 600/494 |

FOREIGN PATENT DOCUMENTS

EP 1 203 557 A2 5/2002

* cited by examiner

*Primary Examiner*—Max F. Hindenburg
*Assistant Examiner*—Patricia C Mallari
(74) *Attorney, Agent, or Firm*—Oliff & Berridge, PLC

(57) ABSTRACT

An apparatus for automatically measuring a blood pressure of a living subject, including a cuff which is wound around a portion of the subject, a cuff pulse wave occurring to the cuff when a pressure in the cuff is changed, a pulse-wave detecting device which is worn on another portion of the subject and detects a volumetric pulse wave, a correction-factor determining device for iteratively determining, for each of respective pulses of the volumetric pulse wave, a correction factor to correct an amplitude of the each pulse to a predetermined value, a first determining device for iteratively multiplying, by the correction factor determined for the each of the pulses of the volumetric pulse wave, an amplitude of one of the pulses of the cuff pulse wave that corresponds to the each pulse of the volumetric pulse wave, and thereby determining a corrected amplitude of the one pulse of the cuff pulse wave, and a second determining device for determining a blood pressure of the subject based on a change of the respective corrected amplitudes of the respective pulses of the cuff pulse wave, with respect to the pressure of the cuff.

11 Claims, 12 Drawing Sheets

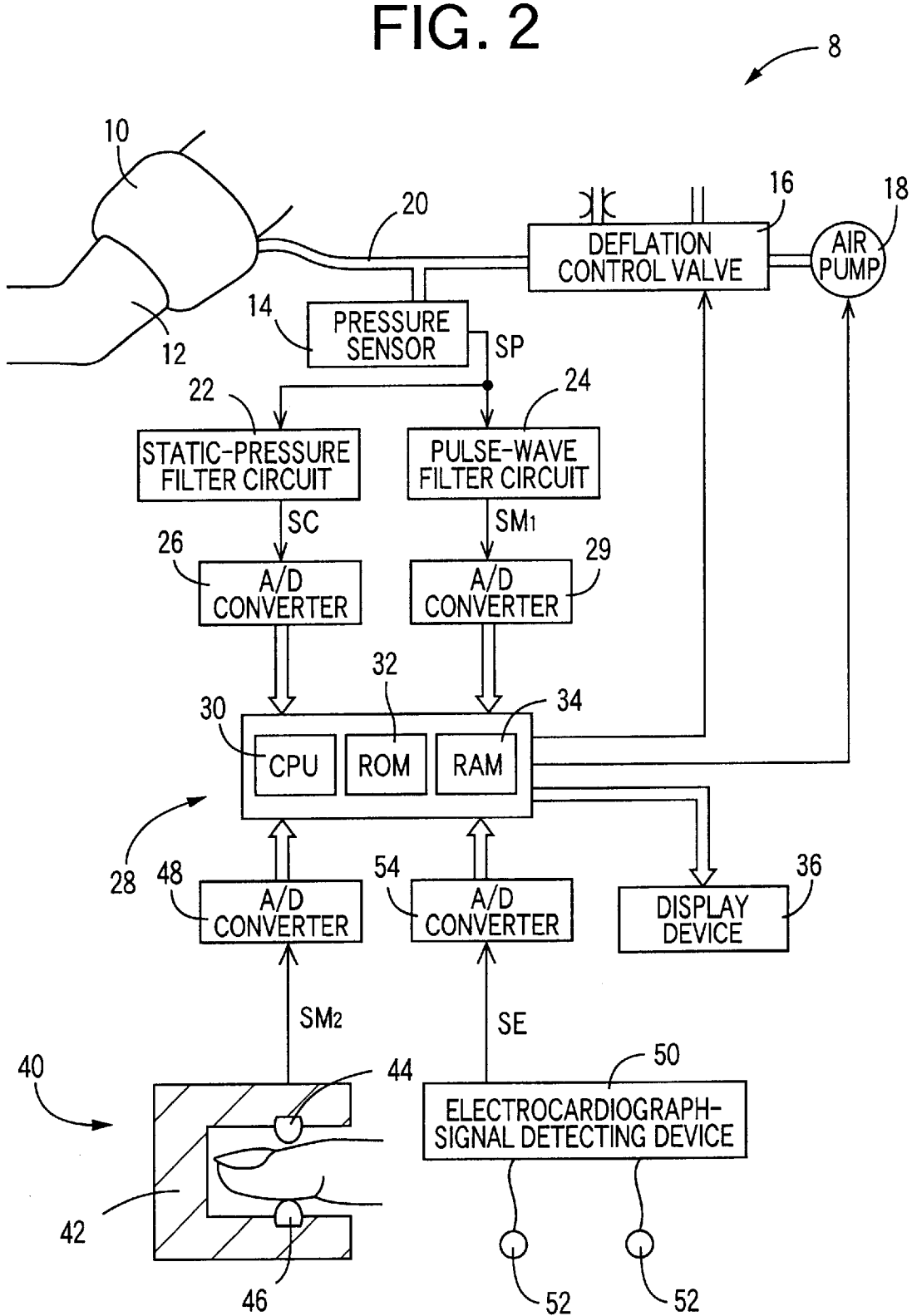

AUTOMATIC BLOOD-PRESSURE MEASURING APPARATUS

BACKGROUND OF THE INVENTION

1. Field of the Invention

The present invention relates to an apparatus for automatically measuring a blood pressure of a living subject according to so-called oscillometric method.

2. Related Art Statement

The oscillometric blood-pressure measuring method is carried out as follows: A pressing pressure of an inflatable cuff which is wound around, e.g., an upper arm of a living subject, that is, a cuff pressure is slowly changed, and a blood pressure of the subject is determined based on the change of an oscillatory component occurring to the cuff during the changing of the cuff pressure (i.e., the change of respective amplitudes of respective heartbeat-synchronous pulses of a cuff pulse wave with respect to the change of cuff pressure). An automatic blood-pressure measuring apparatus which employs the oscillometric method can measure a blood pressure at a front neck, a finger, or an inferior limb of a living subject where it is difficult to measure a blood pressure according to a microphone-using method. In addition, the microphone-using method requires a microphone to be accurately positioned on an artery of the subject, whereas the oscillometric method just needs the cuff to be wound around a portion of the subject. Thus, the oscillometric method can be easily carried out by both skilled and non-skilled operators. Moreover, the oscillometric method can be carried out at a noisy place, or on a child or an in-shock patient who produces small Korotkoff sounds only. Thus, the oscillometric-type automatic blood-pressure measuring devices have come into wide use.

However, according to the oscillometric method, a blood pressure is determined based on the change of respective amplitudes of respective pulses of the cuff pulse wave occurring to the cuff during the slow changing of cuff pressure, on the assumption that the blood pressure of the subject does not change during the changing of cuff pressure. More specifically described, it is assumed that respective amplitudes A, and respective prescribed points, such as minimal values (i.e., diastolic pressures) or maximal values (i.e., systolic pressures), of respective pulses of a blood-pressure wave, shown in FIG. 1A, do not change during the changing of cuff pressure.

However, in an actual blood-pressure measurement, the cardiac output of the subject may change during the changing of cuff pressure, so that as shown in FIG. 1B, the respective amplitudes A of respective pulses of the blood-pressure wave may change, or so that as shown in FIG. 1C, the amplitudes A may not change but the blood pressure values may change. In some cases, both the amplitudes A and the blood pressure values may change. If the cardiac output or the blood pressure largely changes during the blood-pressure measurement, the envelope of respective amplitudes of respective pulses of the cuff pulse wave with respect to the cuff pressure deforms, which leads to determining an inaccurate blood pressure or even failing to determine a blood pressure.

SUMMARY OF THE INVENTION

It is therefore an object of the present invention to provide an apparatus which automatically measures a blood pressure of a living subject with high accuracy.

The Inventor has carried out extensive studies and found the following facts: When amplitude of a blood-pressure waveform changes, amplitude of a volumetric pulse wave also changes. Therefore, if the same corrections to correct respective amplitudes of a volumetric pulse wave obtained during the changing of pressure of an inflatable cuff, to a predetermined value, are applied to respective amplitudes of a cuff pulse wave occurring to the cuff during the changing of the cuff pressure, an accurate blood pressure can be determined based on the thus corrected amplitudes of the cuff pulse wave. In addition, when blood pressure changes, pulse period also changes. Therefore, if blood pressure values are estimated based on pulse period values obtained during the changing of the cuff pressure, and the same corrections to correct the respective blood pressure values to a predetermined value, are applied to respective values of the cuff pressure at respective times of detection of the pulse period values, an accurate blood pressure can be determined based on the thus corrected values of the cuff pressure. Moreover, if those two inventions are combined, a more accurate blood pressure can be determined. Moreover, if a pulse pressure (i.e., an amplitude of a blood-pressure waveform) is estimated, based on two successive pulse period values obtained during the changing of the cuff pressure, according to a known technique, and the same corrections to correct respective pulse pressure values, determined based on respective pairs of successive pulse period values obtained during the changing of the cuff pressure, to a predetermined value, are applied to respective amplitudes of a cuff pulse wave occurring to the cuff during the changing of the cuff pressure, an accurate blood pressure can be determined based on the thus corrected amplitudes of the cuff pulse wave. Furthermore, if this invention is combined with the above-indicated second invention, a more accurate blood pressure can be determined.

The above object has been achieved by the present invention. According to the first invention, there is provided an apparatus for automatically measuring a blood pressure of a living subject, comprising an inflatable cuff which is adapted to be wound around a first portion of the subject, a cuff pulse wave including a plurality of heartbeat-synchronous pulses occurring to the cuff when a pressure in the cuff is changed; a volumetric-pulse-wave detecting device which is adapted to be worn on a second portion of the subject and which detects, from the second portion of the subject, a volumetric pulse wave including a plurality of heartbeat-synchronous pulses; a correction-factor determining means for iteratively determining, for each of the heartbeat-synchronous pulses of the volumetric pulse wave, a correction factor to correct an amplitude of the each heartbeat-synchronous pulse to a predetermined value; a corrected-cuff-pulse-wave-amplitude determining means for iteratively multiplying, by the correction factor determined by the correction-factor determining means for the each of the heartbeat-synchronous pulses of the volumetric pulse wave, an amplitude of one of the heartbeat-synchronous pulses of the cuff pulse wave that corresponds to the each heartbeat-synchronous pulse of the volumetric pulse wave, and thereby iteratively determining a corrected amplitude of the one heartbeat-synchronous pulse of the cuff pulse wave; and a blood-pressure determining means for determining a blood pressure of the subject based on a change of the respective corrected amplitudes of the respective heartbeat-synchronous pulses of the cuff pulse wave, with respect to the pressure of the cuff.

According to this invention, the correction-factor determining means iteratively determines, for each of the pulses of the volumetric pulse wave detected by the volumetric-pulse-wave detecting device, a correction factor to correct an amplitude of the each pulse to a predetermined value, and the corrected-cuff-pulse-wave-amplitude determining means iteratively multiplies, by the correction factor determined for the each of the pulses of the volumetric pulse wave, an amplitude of one of the pulses of the cuff pulse wave that corresponds to the each pulse of the volumetric pulse wave, and thereby iteratively determines a corrected amplitude of the one pulse of the cuff pulse wave. The thus determined corrected cuff-pulse-wave amplitudes are free of the influence of change of cardiac output of the subject during the changing of pressure of the cuff. And, the blood-pressure determining means determines a blood pressure of the subject based on a change of the respective corrected amplitudes of the respective pulses of the cuff pulse wave, with respect to the pressure of the cuff. Therefore, the thus determined blood pressure enjoys a high accuracy.

According to the second invention, there is provided an apparatus for automatically measuring a blood pressure of a living subject, comprising an inflatable cuff which is adapted to be wound around a portion of the subject, a cuff pulse wave including a plurality of heartbeat-synchronous pulses occurring to the cuff when a pressure in the cuff is changed; a heartbeat-synchronous-wave detecting device which detects, from the subject, a heartbeat-synchronous wave including a plurality of heartbeat-synchronous pulses; a pulse-period determining means for iteratively determining a pulse period of the subject based on a time interval between respective prescribed periodic points of each pair of successive heartbeat-synchronous pulses of the heartbeat-synchronous wave detected by the heartbeat-synchronous-wave detecting device during the changing of the pressure of the cuff an estimated-blood-pressure determining means for iteratively determining an estimated blood pressure of the subject during the changing of the pressure of the cuff, based on each of the pulse periods iteratively determined by the pulse-period determining means, according to a predetermined relationship between estimated blood pressure and pulse period; a blood-pressure-correction-value determining means for iteratively determining, for the each of the pulse periods, a blood-pressure correction value to correct a corresponding one of the estimated blood pressures iteratively determined by the estimated-blood-pressure determining means, to a predetermined value; a corrected-cuff-pressure determining means for subtracting, from a pressure of the cuff at a time of detection of one of the heartbeat-synchronous pulses of the cuff pulse wave that corresponds to the each of the pulse periods, the blood-pressure correction value determined by the blood-pressure-correction-value determining means for the each of the pulse periods, and thereby determining a corrected pressure of the cuff for the each of the pulse periods; and a blood-pressure determining means for determining a blood pressure of the subject based on a change of respective amplitudes of the respective heartbeat-synchronous pulses of the cuff pulse wave, with respect to the respective corrected pressures of the cuff determined by the corrected-cuff-pressure determining means for the respective pulse periods.

According to this invention, the estimated-blood-pressure determining means iteratively determines an estimated blood pressure of the subject during the changing of the pressure of the cuff, based on each of the pulse periods, and the blood-pressure-correction-value determining means iteratively determines, for the each of the pulse periods, a blood-pressure correction value to correct a corresponding one of the estimated blood pressures, to a predetermined value. The corrected-cuff-pressure determining means subtracts, from a pressure of the cuff at a time of detection of one of the pulses of the cuff pulse wave that corresponds to the each of the pulse periods, the blood-pressure correction value determined for the each of the pulse periods, and thereby determines a corrected pressure of the cuff for the each of the pulse periods. The thus determined corrected pressure values of the cuff would be detected at respective times of detection of respective pulses of the cuff pulse wave in a state in which there would be no influence of change of blood pressure of the subject during the changing of the cuff pressure. And, the blood-pressure determining means determines a blood pressure of the subject based on a change of respective amplitudes of the respective pulses of the cuff pulse wave, with respect to the respective corrected pressure values of the cuff determined by the corrected-cuff-pressure determining means. Therefore, the thus determined blood pressure enjoys a high accuracy.

According to the third invention, there is provided an apparatus for automatically measuring a blood pressure of a living subject, comprising an inflatable cuff which is adapted to be wound around a first portion of the subject, a cuff pulse wave including a plurality of heartbeat-synchronous pulses occurring to the cuff when a pressure in the cuff is changed; a volumetric-pulse-wave detecting device which is adapted to be worn on a second portion of the subject and which detects, from the second portion of the subject, a volumetric pulse wave including a plurality of heartbeat-synchronous pulses; a correction-factor determining means for iteratively determining, for each of the heartbeat-synchronous pulses of the volumetric pulse wave, a correction factor to correct an amplitude of the each heartbeat-synchronous pulse to a predetermined value; a corrected-cuff-pulse-wave-amplitude determining means for iteratively multiplying, by the correction factor determined by the correction-factor determining means for the each of the heartbeat-synchronous pulses of the volumetric pulse wave, an amplitude of one of the heartbeat-synchronous pulses of the cuff pulse wave that corresponds to the each heartbeat-synchronous pulse of the volumetric pulse wave, and thereby iteratively determining a corrected amplitude of the one heartbeat-synchronous pulse of the cuff pulse wave; a heartbeat-synchronous-wave detecting device which detects, from the subject, a heartbeat-synchronous wave including a plurality of heartbeat-synchronous pulses; a pulse-period determining means for iteratively determining a pulse period of the subject based on a time interval between respective prescribed periodic points of each pair of successive heartbeat-synchronous pulses of the heartbeat-synchronous wave detected by the heartbeat-synchronous-wave detecting device during the changing of the pressure of the cuff, an estimated-blood-pressure determining means for iteratively determining an estimated blood pressure of the subject during the changing of the pressure of the cuff, based on each of the pulse periods iteratively determined by the pulse-period determining means, according to a predetermined relationship between estimated blood pressure and pulse period; a blood-pressure-correction-value determining means for iteratively determining, for the each of the pulse periods, a blood-pressure correction value to correct a corresponding one of the estimated blood pressures iteratively determined by the estimated-blood-pressure determining means, to a predetermined value; a corrected-cuff-pressure determining means for subtracting, from a pressure of the cuff at a time of detection of one of the heartbeat-synchronous pulses of the cuff pulse wave that corresponds to the each of the pulse periods, the blood-pressure correction value determined by the blood-pressure-correction-value determining means for the each of the pulse periods, and thereby determining a corrected pressure of the cuff for the each of the pulse periods; and a blood-pressure determining means for determining a blood pressure of the subject based on a change of the respective corrected amplitudes of the respective heartbeat-synchronous pulses of the cuff pulse wave determined by the corrected-cuff-pulse-wave-amplitude determining means, with respect to the respective corrected pressures of the cuff determined by the corrected-cuff-pressure determining means for the respective pulse periods.

According to this invention, the blood-pressure determining means determines a blood pressure of the subject based on a change of the respective corrected amplitudes of the respective pulses of the cuff pulse wave, with respect to the respective corrected pressures of the cuff. Since the corrected pressure values of the cuff would be detected at respective times of detection of respective pulses of the cuff pulse wave in a state in which there would be no influence of change of blood pressure of the subject during the changing of the cuff pressure, and the corrected cuff-pulse-wave amplitudes are free of the influence of change of cardiac output of the subject during the changing of pressure of the cuff, the determined blood pressure enjoys a higher accuracy.

According to the fourth invention, there is provided an apparatus for automatically measuring a blood pressure of a living subject, comprising an inflatable cuff which is adapted to be wound around a portion of the subject, a cuff pulse wave including a plurality of heartbeat-synchronous pulses occurring to the cuff when a pressure in the cuff is changed; a heartbeat-synchronous-wave detecting device which detects, from the subject, a heartbeat-synchronous wave including a plurality of heartbeat-synchronous pulses; a pulse-period determining means for iteratively determining a pulse period of the subject based on a time interval between respective prescribed periodic points of each pair of successive heartbeat-synchronous pulses of the heartbeat-synchronous wave detected by the heartbeat-synchronous-wave detecting device during the changing of the pressure of the cuff; an estimated-pulse-pressure determining means for iteratively determining, for each of the pulse periods iteratively determined by the pulse-period determining means, an estimated pulse pressure of the subject during the changing of the pressure of the cuff, based on each pair of successive pulse periods of the pulse periods, according to a predetermined relationship between pulse pressure and a pair of successive pulse periods; a correction-factor determining means for iteratively determining, for each of the estimated pulse pressures iteratively determined by the estimated pulse pressure determining means, a correction factor to correct the each estimated pulse pressure to a predetermined value; a corrected-cuff-pulse-wave-amplitude determining means for iteratively multiplying, by the correction factor determined by the correction-factor determining means for the each of the estimated pulse pressures, an amplitude of one of the heartbeat-synchronous pulses of the cuff pulse wave that corresponds to the each of the estimated pulse pressures, and thereby iteratively determining a corrected amplitude of the one heartbeat-synchronous pulse of the cuff pulse wave; and a blood-pressure determining means for determining a blood pressure of the subject based on a change of the respective corrected amplitudes of the respective heartbeat-synchronous pulses of the cuff pulse wave, with respect to the pressure of the cuff.

According to this invention, the correction-factor determining means iteratively determines, for each of the estimated pulse pressures iteratively determined by the estimated pulse pressure determining means, a correction factor to correct the each estimated pulse pressure to a predetermined value, and the corrected-cuff-pulse-wave-amplitude determining means iteratively multiplies, by the correction factor determined for the each of the estimated pulse pressures, an amplitude of one of the pulses of the cuff pulse wave that corresponds to the each of the estimated pulse pressures, and thereby iteratively determines a corrected amplitude of the one pulse of the cuff pulse wave. The thus determined corrected cuff-pulse-wave amplitudes are free of the influence of change of cardiac output of the subject during the changing of pressure of the cuff. And, the blood-pressure determining means determines a blood pressure of the subject based on a change of the respective corrected amplitudes of the respective pulses of the cuff pulse wave, with respect to the pressure of the cuff. Therefore, the determined blood pressure enjoys a higher accuracy.

According to the fifth invention, there is provided an apparatus for automatically measuring a blood pressure of a living subject, comprising an inflatable cuff which is adapted to be wound around a first portion of the subject, a cuff pulse wave including a plurality of heartbeat-synchronous pulses occurring to the cuff when a pressure in the cuff is changed; a heartbeat-synchronous-wave detecting device which detects, from the subject, a heartbeat-synchronous wave including a plurality of heartbeat-synchronous pulses; a pulse-period determining means for iteratively determining a pulse period of the subject based on a time interval between respective prescribed periodic points of each pair of successive heartbeat-synchronous pulses of the heartbeat-synchronous wave detected by the heartbeat-synchronous-wave detecting device during the changing of the pressure of the cuff, an estimated-pulse-pressure determining means for iteratively determining, for each of the pulse periods iteratively determined by the pulse-period determining means, an estimated pulse pressure of the subject during the changing of the pressure of the cuff, based on each pair of successive pulse periods of the pulse periods, according to a predetermined relationship between pulse pressure and a pair of successive pulse periods; a correction-factor determining means for iteratively determining, for each of the estimated pulse pressures iteratively determined by the estimated pulse pressure determining means, a correction factor to correct the each estimated pulse pressure, to a predetermined value; a corrected-cuff-pulse-wave-amplitude determining means for iteratively multiplying, by the correction factor determined by the correction-factor determining means for the each of the estimated pulse pressures, an amplitude of one of the heartbeat-synchronous pulses of the cuff pulse wave that corresponds to the each of the estimated pulse pressures, and thereby iteratively determining a corrected amplitude of the one heartbeat-synchronous pulse of the cuff pulse wave; an estimated-blood-pressure determining means for iteratively determining an estimated blood pressure of the subject during the changing of the pressure of the cuff, based on the each of the pulse periods iteratively determined by the pulse-period determining means, according to a predetermined relationship between estimated blood pressure and pulse period; a blood-pressure-correction-value determining means for iteratively determining, for the each of the pulse periods, a blood-pressure correction value to correct a corresponding one of the estimated blood pressures iteratively determined by the estimated-blood-pressure determining means, to a predetermined value; a corrected-cuff-pressure determining means for subtracting, from a pressure of the cuff at a time of detection of one of the heartbeat-synchronous pulses of the cuff pulse wave that corresponds to the each of the pulse periods, the blood-pressure correction value determined by the blood-pressure-correction-value determining means for the each of the pulse periods, and thereby determining a corrected pressure of the cuff for the each of the pulse periods; and a blood-pressure determining means for determining a blood pressure of the subject based on a change of the respective corrected amplitudes of the respective heartbeat-synchronous pulses of the cuff pulse wave determined by the corrected-cuff-pulse-wave-amplitude determining means, with respect to the respective corrected pressures of the cuff determined-by the corrected-cuff-pressure determining means for the respective pulse periods.

According to this invention, the blood-pressure determining means determines a blood pressure of the subject based on a change of the respective corrected amplitudes of the respective pulses of the cuff pulse wave, with respect to the respective corrected pressures of the cuff. Since the corrected pressure values of the cuff would be detected at respective times of detection of respective pulses of the cuff pulse wave in a state in which there would be no influence of change of blood pressure of the subject during the changing of the cuff pressure, and the corrected cuff-pulse-wave amplitudes are free of the influence of change of cardiac output of the subject during the changing of pressure of the cuff, the determined blood pressure enjoys a higher accuracy.

BRIEF DESCRIPTION OF THE DRAWINGS

The above and optional objects, features, and advantages of the present invention will be better understood by reading the following detailed description of the preferred embodiments of the invention when considered in conjunction with the drawings, in which:

FIG. 2 is a diagrammatic view for explaining a construction of an automatic blood-pressure measuring apparatus to which the present invention is applied;

DETAILED DESCRIPTION OF PREFERRED EMBODIMENTS

Figure 1A:
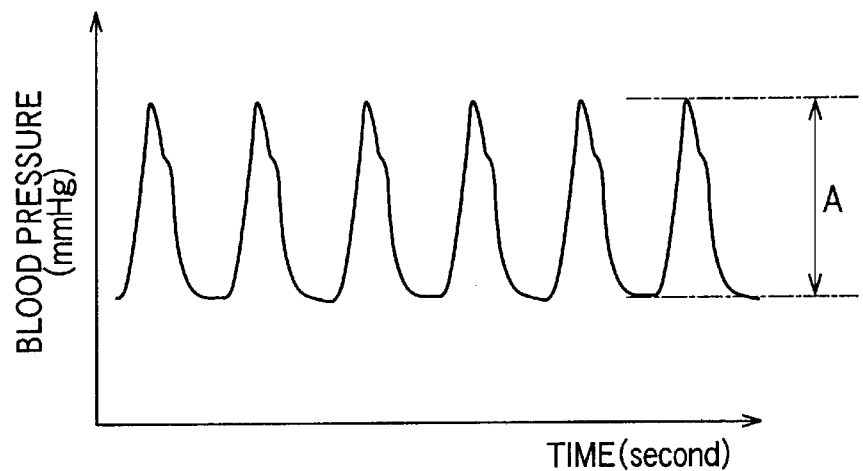
FIG. 1A is a graph of a blood-pressure waveform that does not change.
Figure 1B:
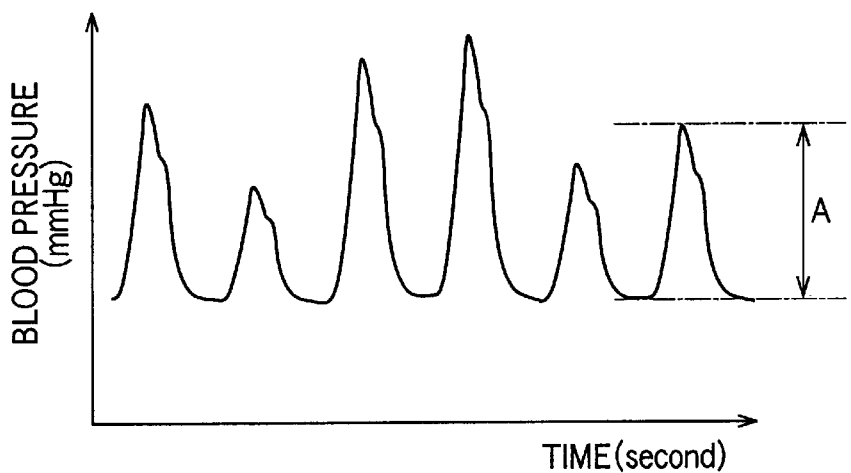
FIG. 1B is a graph of a blood-pressure waveform indicating that amplitudes A change.
Figure 1C:
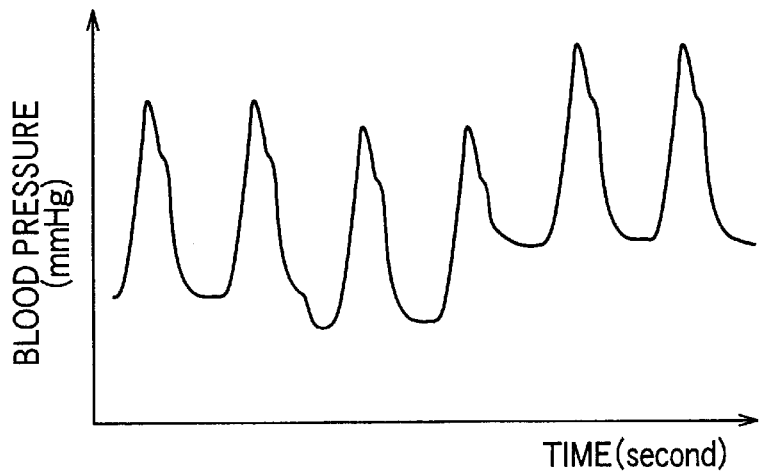
FIG. 1C is a graph of a blood-pressure waveform indicating that blood pressure changes.

Hereinafter, there will be described a preferred embodiment of the present invention in detail by reference to the drawings. FIG. 2 shows a diagrammatic view for explaining a construction of an automatic blood-pressure measuring apparatus 8 to which the present invention is applied.

In FIG. 2, reference numeral 10 designate an inflatable cuff which includes a belt-like cloth bag and a rubber bag accommodated in the cloth bag and which is adapted to be wound around, e.g., a right upper arm 12 of a patient as a living subject. The cuff 10 is connected to a pressure sensor 14, a deflation control valve 16, and an air pump 18 via a piping 20. The deflation control valve 16 is selectively placed in a pressure-supply position in which the control valve 16 permits a pressurized air to be supplied from the air pump 18 to the cuff 10, a slow-deflation position in which the control valve 16 permits the pressurized air to be slowly discharged from the cuff 10, and a quick-deflation position in which the control valve 16 permits the pressurized air to be quickly discharged from the cuff 10.

The pressure sensor 14 detects an air pressure $P_K$ in the cuff 10, and supplies a pressure signal SP representing the detected pressure $P_K$, to each of a static-pressure filter circuit 22 and a pulse-wave filter circuit 24. The static-pressure filter circuit 22 includes a low-pass filter and extracts, from the pressure signal SP, a static-pressure component contained in the pressure signal SP, i.e., a cuff pressure signal SC representing the static pressure in the cuff 10. The cuff pressure signal SC is supplied to a control device 28 via an analog-to-digital (A/D) converter 26. The pulse-wave filter circuit 24 includes a band-pass filter and extracts, from the pressure signal SP, an oscillating component having predetermined frequencies, i.e., a cuff-pulse-wave signal $SM_1$. The cuff-pulse-wave signal $SM_1$ is supplied to the control device 28 via an A/D converter 29. The cuff-pulse-wave signal $SM_1$ represents a cuff pulse wave $W_K$, i.e., a pressure pulse wave or an oscillatory pressure wave which is produced from a brachial artery, not shown, of the upper arm 12 of the patient in synchronism with the heartbeat of the patient and is propagated to the cuff 10.

The control device 28 is provided by a so-called microcomputer including a central processing unit (CPU) 30, a read only memory (ROM) 32, a random access memory (RAM) 34 and an input-and-output (I/O) port, not shown. The CPU 30 processes signals according to the control programs pre-stored in the ROM 32 by utilizing the temporary-storage function of the RAM 34, and supplies drive signals via the I/O port to respective drive circuits, not shown, associated with the deflation control valve 16 and the air pump 18 so as to change the air pressure in the cuff 10 and perform an oscillometric blood-pressure measuring operation to measure a blood-pressure value BP of the patient, such as a systolic blood-pressure value $BP_{SYS}$ and/or a diastolic blood-pressure value $BP_{DIA}$. In addition, the CPU 30 operates a display device 36 to display the thus measured blood-pressure value BP. The display device 36 may include a cathode ray tube (CRT).

The measuring apparatus 8 further includes a photoelectric-pulse-wave sensor 40 functioning as a volumetric-pulse-wave detecting device. The sensor 40 detects a volumetric pulse wave (i.e., a plethysmogram) representing a volume of blood present in peripheral blood vessels of the subject. The sensor 40 is worn on, e.g., an end portion of a finger of the other arm than the arm around which the cuff 10 is wound. The photoelectric-pulse-wave sensor 40 has the same construction as that of a known sensor used to detect pulse rate. More specifically described, the sensor 40 includes a housing 42 that can accommodate a portion of a living subject, such as an end portion of a finger; a light emitting element 44 as a light source that is disposed on one of opposite walls of the housing 42 and emits, toward the skin of the subject, a red or infrared light in a frequency range that is reflected by hemoglobin, preferably a light having a wavelength of, e.g., about 800 nm, that is not influenced by blood oxygen saturation; and a light receiving element 46 that is disposed on the other wall of the housing 42 such that the light receiving element 46 is opposed to the light emitting element 44, and detects the light transmitted through the portion of the subject. The light receiving element 46 produces a photoelectric-pulse-wave signal $SM_2$ representing the detected amount of light, i.e., volume of blood present in capillaries of the portion of the subject, and supplies the photoelectric-pulse-wave signal $SM_2$ to the control device 28 via an A/D converter 48.

Figure 3:
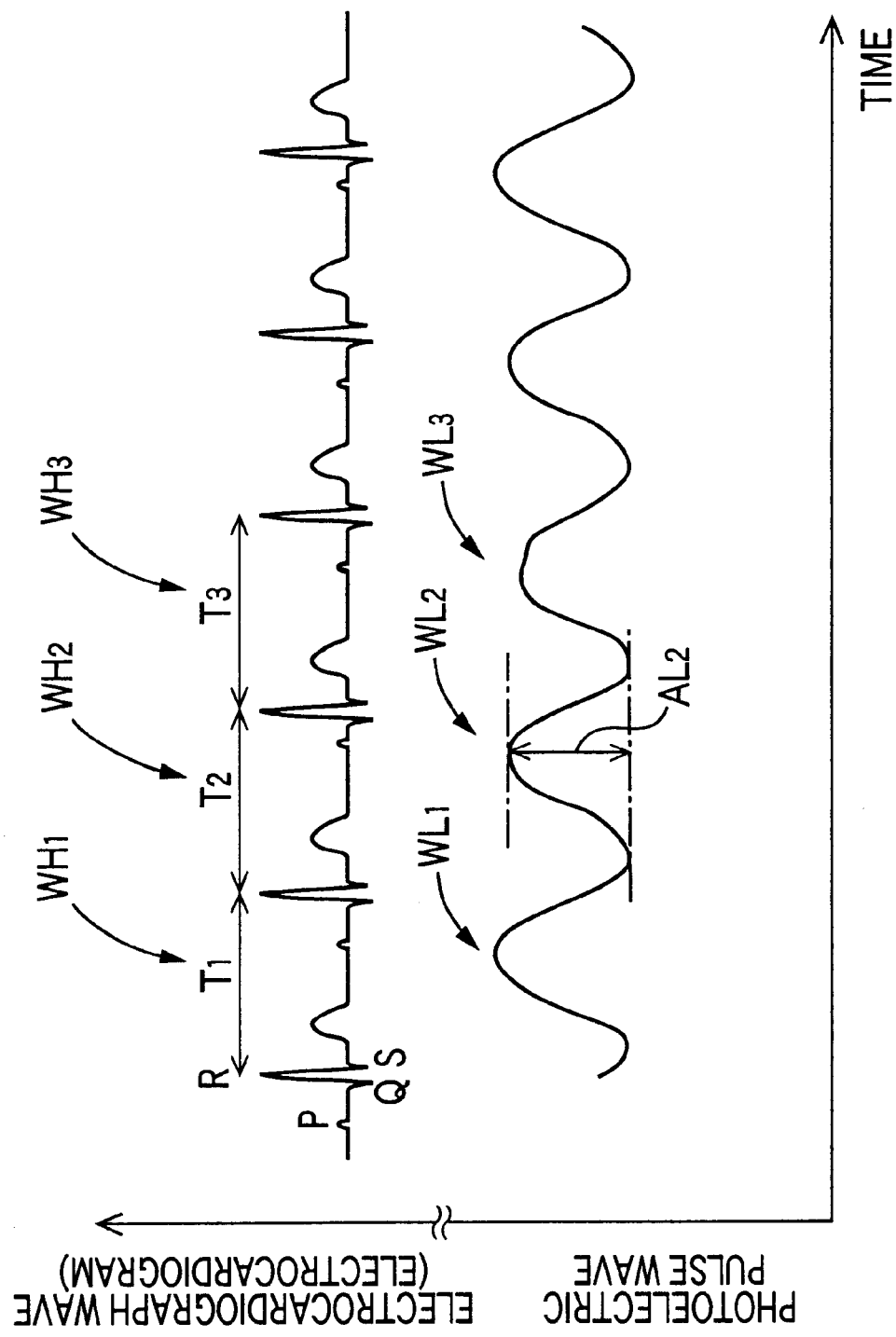
FIG. 3 is a graph showing respective examples of a photoelectric pulse wave detected by a photoelectric-pulse-wave sensor and an electrocardiograph wave detected by an electrocardiograph-signal detecting device.

The measuring apparatus 8 further includes an electrocardiograph (ECG) signal detecting device 50 which continuously detects an ECG wave $WH_n$ (n is a natural number), i.e., so-called electrocardiogram (ECG) representing an action potential of cardiac muscle of the subject, through a plurality of electrodes 52 which are adapted to be adhered to respective prescribed locations of chest of the subject, and supplies an ECG signal SE representing the detected ECG wave $WH_n$, to the control device 28 via an A/D converter 54. Since the ECG wave $WH_n$ is a heartbeat-synchronous wave that is produced in synchronism with the heartbeat of the subject, the ECG signal detecting device 50 functions as a heartbeat-synchronous-wave detecting device. FIG. 3 shows respective examples of a photoelectric pulse wave $WL_n$ detected by the photoelectric-pulse-wave sensor 40 and an ECG wave $WH_n$ detected by the ECG signal detecting device 50. As shown in FIG. 3, each of heartbeat-synchronous pulses of the ECG wave $WH_n$ includes a P-wave, a Q-wave, an R-wave, and an S-wave.

Figure 4:
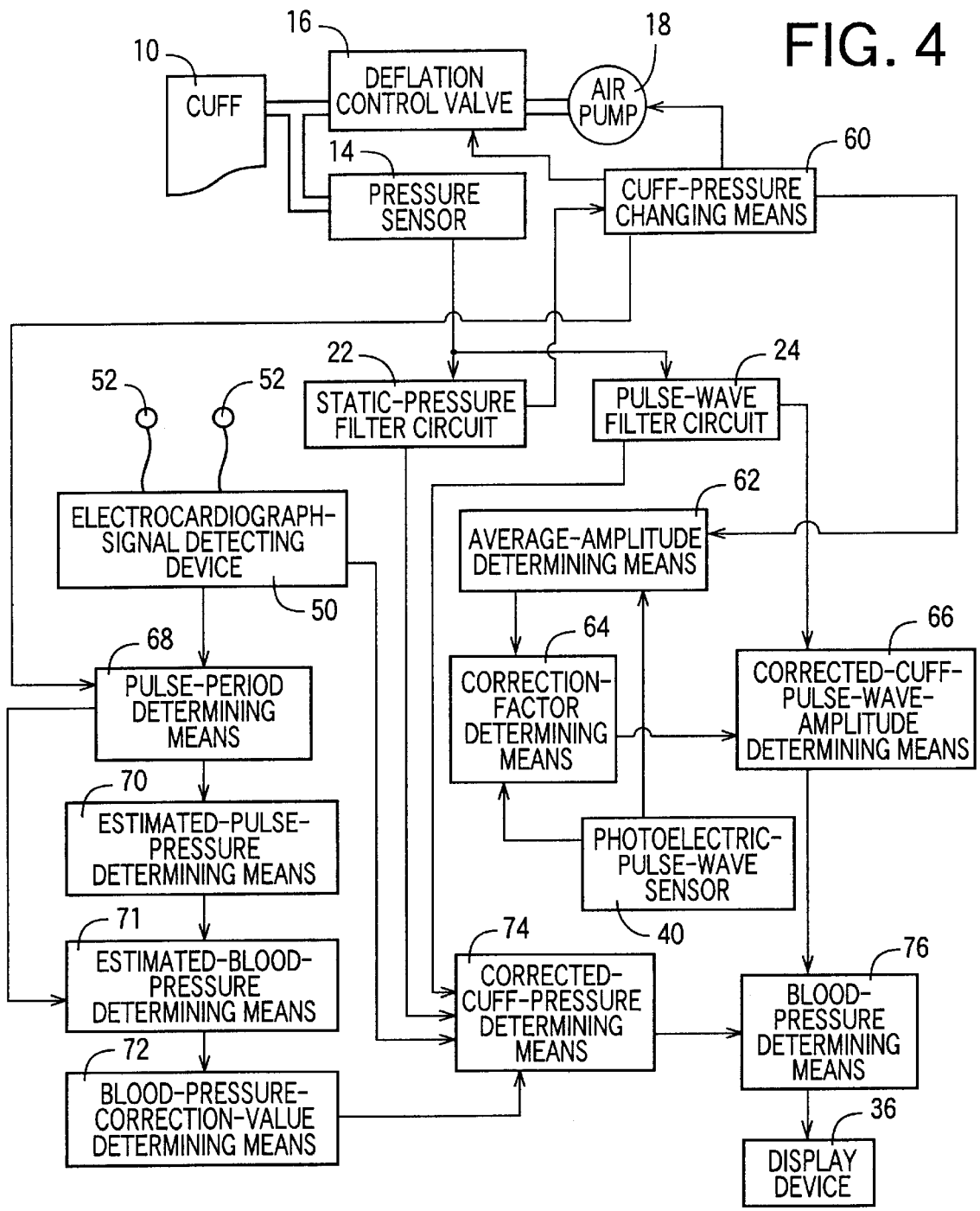
FIG. 4 is a block diagram for explaining essential functions of a control device of the automatic blood-pressure measuring apparatus of FIG. 2.

FIG. 4 is a block diagram for explaining essential functions of the control device 28. In the figure, a cuff-pressure changing means 60 operates, based on the cuff pressure signal SC supplied from the static-pressure filter circuit 22, the air pump 18 and the deflation control valve 16 to quickly increase the pressing pressure of the cuff 10, i.e., the cuff pressure $P_C$ up to a prescribed first target pressure $P_{CM1}$ (e.g., 180 mmHg) which would be higher than a systolic blood-pressure value $BP_{SYS}$ of the patient and subsequently slowly decrease the cuff pressure $P_C$, at a rate of from 2 to 3 mmHg/sec, down to a prescribed second target pressure $P_{CM2}$ (e.g., 60 mmHg) which would be lower than a diastolic blood-pressure value $BP_{DIA}$ of the patient.

An average-amplitude determining means 62 determines respective amplitudes $AL_n$ of the respective heartbeat-synchronous pulses $WL_n$ of the photoelectric pulse wave which is continuously detected by the photoelectric-pulse-wave sensor 40 while the cuff pressure $P_C$ is slowly decreased by the cuff-pressure changing means 60, and additionally determines an average $AL_{per}$ of the thus determined amplitudes $AL_n$. Here, as shown in FIG. 3, a difference between a maximal value and a minimal value of each heartbeat-synchronous pulse $WL_n$ of the photoelectric pulse wave is defined as an amplitude $AL_n$ of the each pulse $WL_n$.

A correction-factor determining means 64 determines, for each heartbeat-synchronous pulse $WL_n$ of the photoelectric pulse wave detected by the photoelectric-pulse-wave 40, a correction factor $K_n$ as a ratio of the average amplitude $AL_{per}$ determined by the average-amplitude determining means 62, to the amplitude $AL_n$ of the each pulse $WL_n$, according to the following expression (1):

$$K_n = AL_{per}/AL_n \tag{1}$$

Since the average amplitude $AL_{per}$ is obtained by multiplying the amplitude $AL_n$ of the each pulse $WL_n$ by the correction factor $K_n$, the correction factor $K_n$ is a factor for correcting the amplitude $AL_n$ of the each pulse $WL_n$ to a predetermined value (i.e., the average amplitude $AL_{per}$).

A corrected-cuff-pulse-wave-amplitude determining means 66 multiplies an amplitude $AK_n$ of each of respective heartbeat-synchronous pulses $WK_n$ of the cuff pulse wave that respectively correspond to the respective heartbeat-synchronous pulses $WL_n$ of the photoelectric pulse wave, by the correction factor $K_n$ determined for a corresponding one of the pulses $WL_n$ by the correction-factor determining means 64, and thereby determines a corrected amplitude $AK_n'$ of the each heartbeat-synchronous pulse $WK_n$ of the cuff pulse wave, according to the following expression (2):

$$AK_n' = AK_n \times K_n \tag{2}$$

The each pulse $WK_n$ of the cuff pulse wave and the corresponding pulse $WL_n$ of the photoelectric pulse wave are produced by a same heartbeat of the patient. In the case where the cuff 10 is worn on the patient at the position which is more proximal to the heart of the patient than the position where the photoelectric-pulse-wave sensor 40 is worn, the each pulse $WK_n$ of the cuff pulse wave is followed by the corresponding pulse $WL_n$ of the photoelectric pulse wave.

As described above, the correction factor $K_n$ determined by the correction-factor determining means 64 is a factor for correcting the amplitude $AL_n$ of each pulse $WL_n$ of the photoelectric pulse wave to a predetermined value. That is, the correction factors $K_n$ are factors for removing respective fluctuations of the respective amplitudes $AL_n$ of the respective pulses $WL_n$ of the photoelectric pulse wave detected during the slow decreasing of the cuff pressure $P_C$. It can be speculated that the same fluctuations of amplitudes would commonly occur to both the photoelectric pulse wave detected at the position where the photoelectric-pulse-wave sensor 40 is worn and the cuff pulse wave detected at the position where the cuff 10 is worn. Therefore, the respective corrected amplitudes $AK_n'$ of the respective heartbeat-synchronous pulses $WK_n$ of the cuff pulse wave, obtained by multiplying the respective amplitudes $AK_n$ of the pulses $WK_n$ by the corresponding correction factors $K_n$, are free of the respective fluctuations of the amplitudes $AK_n$ of the pulses $WK_n$ detected during the slow decreasing of the cuff pressure $P_C$.

A pulse-period determining means 68 determines, based on the ECG wave $WH_n$ detected by the ECG-signal detecting device 50 during the slow decreasing of the cuff pressure $P_C$ under the control of the cuff-pressure changing means 60, a pulse period $T_n$ (seconds), i.e., a time interval between respective prescribed periodic portions of each pair of successive heartbeat-synchronous pulses of the ECG wave $WH_n$. For example, the pulse-period determining means 68 determines, as each pulse period $T_n$, a time interval between respective R-waves of each pair of successive pulses $WH_n$, $WH_{n+1}$, of the ECG wave.

Figure 5:
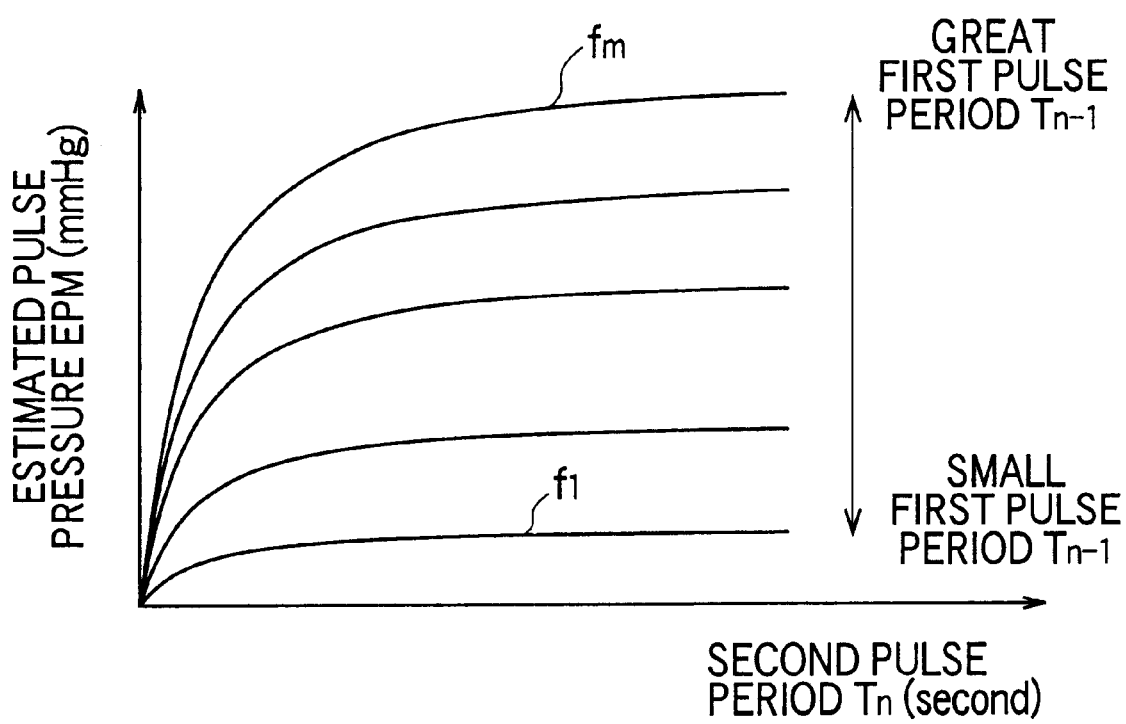
FIG. 5 is a graph showing a relationship between estimated pulse pressure EPM and two successive pulse periods T.

An estimated-pulse-pressure determining means 70 employs a predetermined relationship, shown in FIG. 5, among estimated pulse pressure EPM and two successive pulse periods T successively determined by the pulse-period determining means 68, and determines, for each of the pulse periods $T_n$ successively determined, an estimated pulse pressure EPM at the time of detection of each pulse $WH_{n+1}$ of the ECG wave, based on each pair of successive pulse periods $T_{n-1}$, $T_n$.

The relationship shown in FIG. 5 is experimentally determined, in advance, and is used in the following manner: First, one curve is selected, based on the first one $T_{n-1}$ of each pair of actually determined successive pulse periods $T_{n-1}$, $T_n$ (hereinafter, referred to as the first pulse period $T_{n-1}$), from a plurality of curves $f_m$ (m=1, 2, 3, . . . ) each of which represents a relationship between estimated pulse pressure EPM and second one $T_n$ of each pair of successive pulse periods $T_{n-1}$, $T_n$, (hereinafter, referred to as second pulse period $T_n$ ). Then, an estimated pulse pressure EPM is determined, according to the thus selected curve $f_m$, based on the actually determined second pulse period $T_n$. The estimated pulse pressure EPM determined according to the relationship shown in FIG. 5 is an estimated pulse pressure EPM at the time of detection of the second one $WH_{n+1}$, of each pair of successive pulses $WH_n$, $WH_{n+1}$ of the ECG wave that are used to determine the actual second pulse period $T_n$.

It can be speculated that the reason why pulse period T and estimated pulse pressure EPM has the relationship shown in FIG. 5 is as follows: The longer the diastolic period of the heart is, the more blood the heart stores. Therefore, in a systolic period after a longer diastolic period, more blood is outputted from the heart. In addition, cardiac output values correspond, one by one, to pulse pressure values PM. Thus, each curve $f_m$ indicates, within a range in which pulse period T is short, a greater estimated pulse pressure EPM corresponds to a longer pulse period T. However, the blood amount that can be stored in the heart has an upper limit, and accordingly the cardiac output has an upper limit. Therefore, each curve fm indicates, in a range in which pulse period T is longer than a certain level, that estimated pulse pressure EPM does not increase any more as pulse period T increases. Meanwhile, if a short first pulse period $T_{n-1}$ occurs because of, e.g., an arrhythmic pulse, the heart starts the following diastolic period before it contracts a sufficient amount in the preceding systolic period corresponding to the first pulse period $T_{n-1}$. Therefore, in the following diastolic period corresponding to a second pulse period $T_n$, the heart expands a little amount only and, in the following systolic period, the heart outputs a little amount of blood only. Thus, the curves $f_m$ indicate, for an arbitrary second pulse period $T_n$, that a smaller estimated pulse pressure EPM corresponds to a shorter first pulse period $T_{n-1}$. However, the total number of the curves $f_m$ is finite because the curves $f_m$ correspond to predetermined first pulse period values $T_{n-1}$, respectively. Hence, one curve corresponding to the predetermined first pulse period $T_{n-1}$, that is the nearest to an actually measured first pulse period $T_{n-1}$ is selected from the curves fm.

An estimated-blood-pressure determining means 71 determines, according to a prescribed relationship between estimated blood pressure EBP and pulse period T, an estimated blood pressure EBP (e.g., an estimated mean blood pressure $EBP_{MEAN}$, an estimated systolic blood pressure $EBP_{SYS}$, an estimated diastolic blood pressure $EBP_{DIA}$, or an estimated middle blood pressure $EBP_{MID}$ as an average of estimated systolic blood pressure $EBP_{SYS}$ and estimated diastolic blood pressure $EBP_{DIA}$) of the patient during the slow decreasing of the cuff pressure $P_C$, based on each of the pulse period values $T_n$ actually determined by the pulse-period determining means 68, or both the each pulse period value $T_n$ and the estimated pulse pressure value EPM determined by the estimated-pulse-pressure determining means 70 for the each pulse period value $T_n$.

Figure 6:
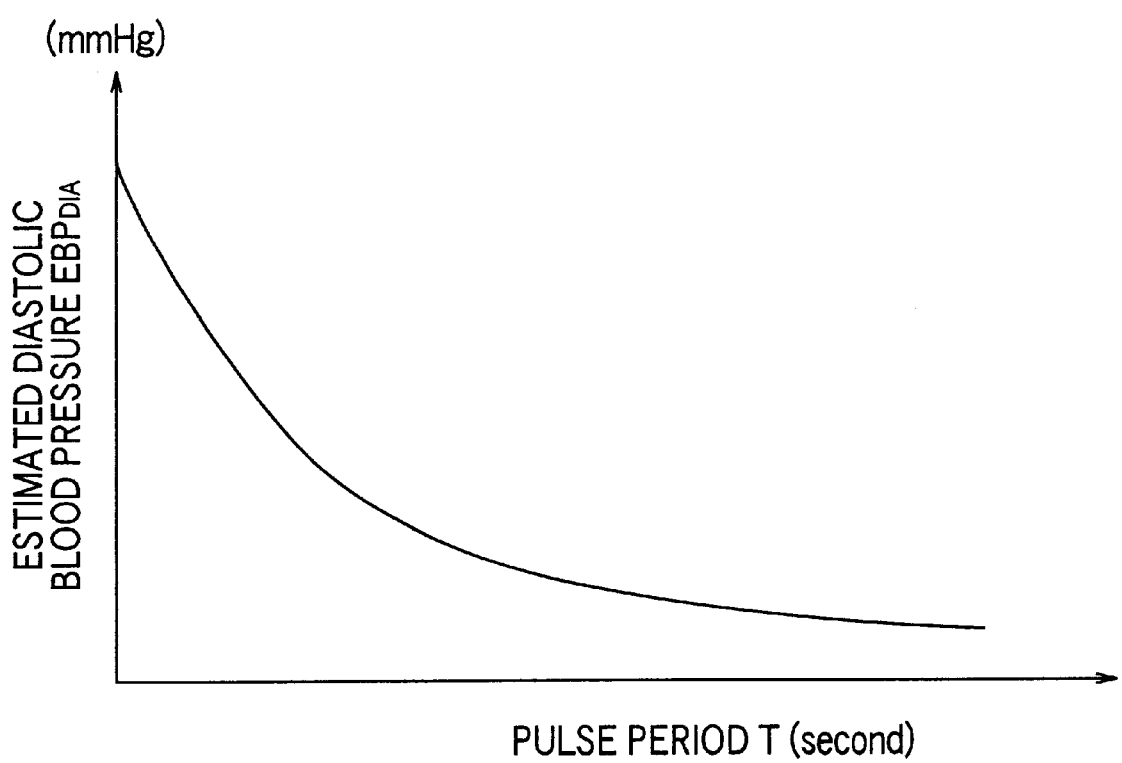
FIG. 6 is a graph showing a predetermined relationship between estimated diastolic blood pressure $EBP_{DIA}$ and pulse period T.

Here, a relationship between blood pressure BP and pulse period T is explained. Blood pressure BP consists of static-pressure component and pulse pressure PM. Thus, blood pressure BP can be obtained by adding pulse pressure PM to the static-pressure component. Diastolic blood pressure $BP_{DIA}$ means blood pressure when the heart is not outputting blood, i.e., the static pressure free of the pulse pressure PM. FIG. 6 shows a relationship between estimated diastolic blood pressure $EBP_{DIA}$ and pulse period T, that is experimentally determined in advance. The reason why estimated diastolic blood pressure $EBP_{DIA}$ and pulse period T has the relationship shown in FIG. 6 is as follows: If a long pulse period T occurs because of an arrhythmic pulse, a long diastolic period also occurs. In addition, since the heart does not output blood in the diastolic period, the blood pressure BP lowers during the diastolic period. Therefore, the longer the pulse period T is, the lower the diastolic blood pressure $BP_{DIA}$ corresponding to the long pulse period T is.

Each of systolic blood pressure $BP_{SYS}$, mean blood pressure $BP_{MEAN}$, and middle blood pressure $BP_{MID}$ is obtained by adding, to diastolic blood pressure $BP_{DIA}$ (i.e., the static pressure), an additional pressure $\alpha$ that is determined based on pulse pressure PM. More specifically described, systolic blood pressure $BP_{SYS}$ is obtained by adding, to diastolic blood pressure $BP_{DIA}$, pulse pressure PM as a whole as additional pressure $\alpha$; and mean blood pressure $BP_{MEAN}$ is obtained by adding, to diastolic blood pressure $BP_{DIA}$, a pressure, as additional pressure $\alpha$, that corresponds to the center of gravity of an area defined by the pulse waveform. Since the pressure corresponding to the center of gravity of area defined by the pulse waveform can approximately be replaced with one third of pulse pressure PM, mean blood pressure $BP_{MEAN}$ is obtained by adding, to diastolic blood pressure $BP_{DIA}$, one third of pulse pressure PM as additional pressure $\alpha$. Middle blood pressure $BP_{MID}$ is obtained by adding, to diastolic blood pressure $BP_{DIA}$, one second of pulse pressure PM as additional pressure $\alpha$. Thus, estimated systolic blood pressure $EBP_{SYS}$, estimated mean blood pressure $EBP_{MEAN}$, and estimated middle blood pressure $EBP_{MID}$ can be determined by using, in place of pulse pressure PM, estimated pulse pressure EPM determined by the estimated-pulse-pressure determining means 70.

In the case where an estimated diastolic blood pressure $EBP_{DIA}$ is determined according to the relationship shown in FIG. 6 based on an actual second pulse period $T_n$, the thus determined, estimated diastolic blood pressure $EBP_{DIA}$ is an estimated diastolic blood pressure $EBP_{DIA}$ at the time of detection of the first one of each pair of consecutive pulses $WH_n$, $WH_{n+1}$ of the ECG wave that are used to determine the actual second pulse period $T_n$. On the other hand, as described above, the estimated pulse pressure EPM determined by the estimated-pulse-pressure determining means 70 according to the relationship shown in FIG. 5 is an estimated pulse pressure EPM at the time of detection of the second one $WH_{+1}$, of the each pair of consecutive pulses $WH_n$, $WH_{n+1}$ that are used to determine the actual second pulse period $T_n$. Thus, in this case, the estimated diastolic blood pressure $EBP_{DIA}$ and the estimated pulse pressure EPM have a time difference corresponding to one heartbeat of the patient. Thus, an estimated systolic blood pressure $EBP_{SYS(n)}$, an estimated mean blood pressure $EBP_{MEAN(n)}$, and an estimated middle blood pressure $EBP_{MID(n)}$, all corresponding to each current pulse period $T_n$, are determined based on an estimated pulse pressure $EPM_n$ determined based on two consecutive pulse periods $T_{n-1}$, $T_{n-2}$ consisting of the last pulse period $T_{n-1}$ preceding the each current pulse period $T_n$ and the second last pulse period $T_{n-2}$ preceding the last pulse period $T_{n-1}$, and an estimated diastolic blood pressure $EBP_{DIA(n)}$ determined based on the each current pulse period $T_n$. The thus determined, estimated blood pressure values $EBP_{SYS(n)}$, etc. are estimated blood pressure values EBP at the time of detection of the first one of each pair of consecutive pulses $WH_n$, $WH_{n+1}$ of the ECG wave that are used to determine the each current pulse period $T_n$.

A blood-pressure-correction-value determining means 72 determines, for each pulse period $T_n$, a blood-pressure correction value $\Delta P_n$ to correct the estimated blood pressure $EBP_n$ determined by the estimated-blood-pressure determining means 71 for the each pulse period $T_n$, into a predetermined value. For example, in the case where estimated middle blood pressure values $EBP_{MID(n)}$ are determined by the estimated-blood-pressure determining means 71, the blood-pressure-correction-value determining means 72 determines an average of the respective estimated middle blood pressure values $EBP_{MID(n)}$, that is, an average estimated middle blood pressure value $MID_{PER}$, and determines, as blood-pressure correction value $\Delta P_n$, a value ($=EBP_{MID(n)}-MID_{PER}$) obtained by subtracting average estimated middle blood pressure value $MID_{PER}$ from each estimated middle blood pressure value $EBP_{MID(n)}$. Since, as explained above, each estimated middle blood pressure value $EBP_{MID(n)}$ is an estimated blood pressure values EBP at the time of detection of the first one of each pair of consecutive pulses $WH_n$, $WH_{n+1}$ of the ECG wave that are used to determine each pulse period $T_n$, each blood-pressure correction value $\Delta P_n$ also relates to the estimated blood pressure values EBP at the time of detection of the first pulse $WH_n$. Therefore, each blood-pressure correction value $\Delta P_n$ means an amount of change of blood pressure BP of the patient at the time of detection of the first one of each pair of consecutive pulses $WH_n$, $WH_{n+1}$, of the ECG wave that are used to determine each pulse period $T_n$, from the average blood pressure BP of the patient during the slow decreasing of the cuff pressure $P_C$.

A corrected-cuff-pressure determining means 74 first identifies one of the heartbeat-synchronous pulses $WK_n$ of the cuff pulse wave that corresponds to each pulse period $T_n$ for which the blood-pressure correction value $\Delta P_n$ has been determined by the blood-pressure-correction-value determining means 72, and subtracts the blood-pressure correction value $\Delta P_n$ from the cuff pressure $P_C$ (hereinafter, referred to as cuff pressure $PRS_n$) at the time of detection of the amplitude $AK_n$ (or peak) of the one pulse $WK_n$, so as to determine a corrected cuff pressure $PRS_n'$. In the case where the blood-pressure correction value $\Delta P_n$ is determined in the above-described manner, the one one pulse $WK_n$ of the cuff pulse wave that corresponds to the each pulse period $T_n$ is one pulse $WK_n$ corresponding to the first one of each pair of consecutive pulses $WH_n$, $WH_{n+1}$ of the ECG wave that are used to determine the each pulse period $T_n$. The each pulse $WH_n$ of the ECG wave and the corresponding pulse $WK_n$ of the cuff pulse wave are produced by a same heartbeat of the patient, as is the case with the corrected-cuff-pulse-amplitude determining means 66.

Here, the meaning of the corrected cuff pressure $PRS_n'$ is explained in more detail. A value ($=PRS_n-EBP_{MID(n)}$) obtained by subtracting, from the cuff-pressure value $PRS_n$ at the time of detection of the amplitude $AK_n$ of each pulse $WK_n$ of the cuff pulse wave, the estimated blood pressure (e.g., the estimated middle blood pressure $EBP_{MID(n)}$ corresponding to the each pulse $WK_n$, can be expressed by the right side of the following expression (3) using the average estimated middle pressure $MID_{per}$:

$$PRS_n - EBP_{MID(n)} = PRS_n - EBP_{MID(n)} + MID_{per} - MID_{per} \quad (3)$$

The right-hand side of the above expression (3) can be rewritten into the following expression (4) or (5):

$$(PRS_n - (EBP_{MID(n)} - MID_{per})) - MID_{per} \quad (4)$$

$$(PRS_n - \Delta P_n) - MID_{per} \quad (5)$$

When the left-hand side of the expression (3) is compared with the expression (4) or (5), the estimated middle blood pressure $EBP_{MID(n)}$ corresponds to the average estimated middle blood pressure $MID_{per}$, and the cuff pressure $PRS_n$ corresponds to the corrected cuff pressure ($PRS_n-\Delta P_n$). Therefore, if the amplitude $AK_n$ of the each cuff pulse observed at the blood pressure $EBP_{MID(n)}$ and the cuff pressure $PRS_n$ is observed at the blood pressure $MID_{per}$, then the cuff pressure should be the corrected cuff pressure ($PRS_n-\Delta P_n$). Thus, the corrected cuff pressure $PRS_n'$ is for correcting the cuff pressure $PRS_n$ at the time of detection of the amplitude $AK_n$ of the each cuff pulse $WK_n$, to a cuff pressure which is free of the influence of the fluctuation of the blood pressure (i.e., the fluctuation of the pulse pressure) of the patient during the slow decreasing of the cuff pressure $P_C$.

A blood-pressure determining means 76 determines a systolic blood-pressure value $BP_{SYS}$, a mean blood-pressure value $BP_{MEAN}$, and a diastolic blood-pressure value $BP_{DIA}$ of the patient, based on the change of the respective corrected cuff-pulse-wave amplitudes $AK_n'$ determined by the corrected-cuff-pulse-wave-amplitude determining means 66, with respect to the respective corrected cuff-pressure values $PRS_n'$ determined by the corrected-cuff-pressure determining means 74, according to an oscillometric blood-pressure determining algorithm. For example, the determining means 76 determines an envelope of the respective corrected cuff-pulse-wave amplitudes $AK_n'$, determines a cuff pressure $P_C$ corresponding to a rising point of the envelope as the systolic blood-pressure value BPsys, and determines a cuff pressure $P_C$ corresponding to a peak point of the envelope as the mean blood-pressure value $BP_{MEAN}$.

Figure 7:
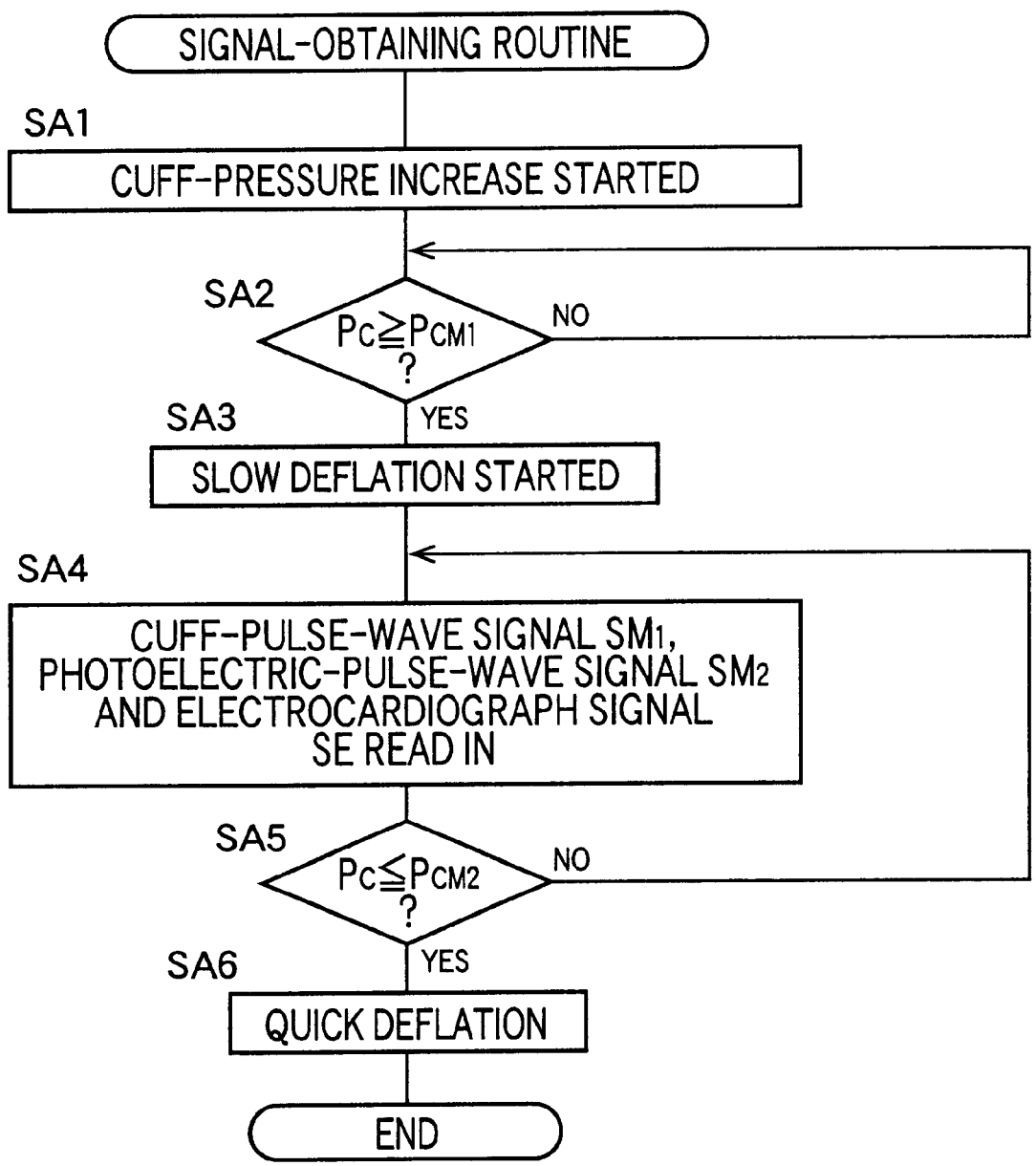
FIG. 7 is a flow chart representing a signal-obtaining routine according to which the control device of FIG. 2 obtains signals to determine a blood pressure BP.
Figure 8:
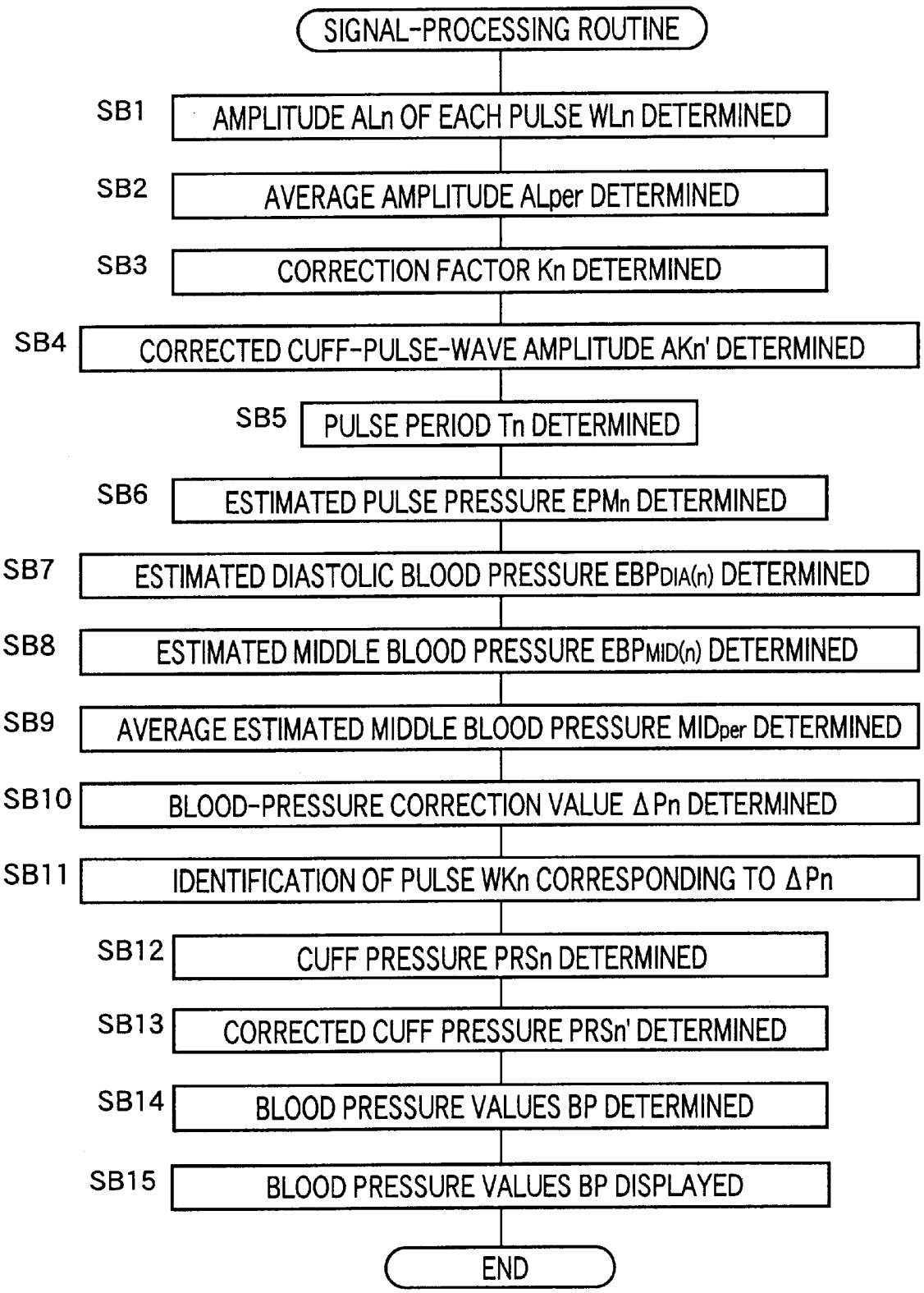
FIG. 8 is a flow chart representing a signal-processing routine according to which the control device of FIG. 2 processes the signals obtained according to the signal-obtaining routine of FIG. 7 and thereby determines the blood pressure.

FIGS. 7 and 8 are flow charts representing essential functions of the control device 28. FIG. 7 shows a signal-obtaining routine for obtaining signals to determine a blood pressure BP of a patient; and FIG. 8 shows a signal-processing routine for processing the signals obtained according to the signal-obtaining routine of FIG. 7 and thereby determining the blood pressure BP.

According to the signal-obtaining routine of FIG. 7, first, the control device 28 carries out Step SA1 (hereinafter, "Step" is omitted, if appropriate) to switch the deflation control valve 16 to its pressure-supply position and operate the air pump 18, so that the pressure in the cuff 10 is quickly increased for a blood-pressure measurement. At SA2, the control device 28 judges whether the cuff pressure $P_C$ has reached a prescribed first target pressure $P_{CM1}$, i.e., 180 mmHg. If a negative judgment is made at SA2, SA2 is repeated till a positive judgment is made. Thus, the increasing of the cuff pressure $P_C$ is continued.

Meanwhile, if the cuff pressure $P_C$ is increased and a positive judgment is made at SA2, the control goes to SA3 to stop the air pump 18 and switch the deflation control valve 16 to its slow-deflation position, so that the pressure in the cuff 10 is slowly decreased at a prescribed rate of 3 mmHg/sec.

At SA4, the control device 28 reads in the cuff-pressure-pulse signal $SM_1$ supplied from the pulse-wave filter circuit 24, the photoelectric-pulse-wave signal $SM_2$ supplied from the photoelectric-pulse-wave sensor 40, and the ECG signal SE supplied from the ECG-signal detecting device 50, each during the slow decreasing of the cuff pressure $P_C$. At SA5, the control device 28 judges whether the cuff pressure $P_C$ has decreased down to a prescribed second target pressure $P_{CM2}$, i.e., 60 mmHg. If a negative judgment is made at SA5, SA4 and SA5 are repeated till a positive judgment is made at Step SA5. Thus, while the cuff pressure $P_C$ is slowly decreased, the control device 28 continues reading in the cuff-pressure-pulse signal $SM_1$, the photoelectric-pulse-wave signal $SM_2$, and the ECG signal SE.

Meanwhile, if a positive judgment is made at SA5, the control goes to SA6 to switch the deflation control valve 16 to its quick-deflation position so that the cuff 10 is quickly deflated. Thus, the signal-obtaining routine is finished. SA1, SA2, SA3, SA5 and SA6 correspond to the cuff-pressure changing means 60.

The signal-obtaining routine is followed by the signal-processing routine shown in FIG. 8. According to the signal-processing routine of FIG. 8, first, the control device 28 carries out SB1 and SB2 corresponding to the average-amplitude determining means 62. At SB1, the control device 28 determines an amplitude $AL_n$ of each of the pulses $WL_n$ of the photoelectric pulse wave read in while SA4 and SA5 of FIG. 7 are repeated and the cuff pressure $P_C$ is slowly decreased. At SB2, the control device 28 determines an average $AL_{per}$ of the respective amplitudes $AL_n$ of the respective pulses $WL_n$, determined at SB1.

Subsequently, at SB3 corresponding to the correction-factor determining means 64, the control device 28 determines a correction factor $K_n$ for each pulse $WL_n$, by dividing the average amplitude $AL_{per}$ determined at SB2, by the amplitude $AL_n$ of the each pulse $WL_n$, determined at SB1, according to the previously-indicated expression (1).

Then, at SB4 corresponding to the corrected-cuff-pulse-wave-amplitude determining means 66, the control device 28 multiplies, by the correction factor $K_n$ determined for each pulse $WL_n$ of the photoelectric pulse wave at SB3, the amplitude $AK_n$ of one of the pulses $WK_n$ of the cuff pulse wave that corresponds to the each pulse $WL_n$, and thereby determines a corrected amplitude $AK_n'$ of the one pulse $WK_n$.

At SB5 corresponding to the pulse-period determining means 68, the control device 28 identifies an R-wave of each of the pulses $WH_n$ of the ECG wave that have been read while Steps SA4 and SA5 of FIG. 7 are repeated and the cuff pressure $P_C$ is slowly decreased, and additionally determines, based on respective distances among the thus determined R-waves, successive pulse period values $T_n$ during the blood pressure measuring operation. Then, at SB6 corresponding to the estimated-pulse-pressure determining means 70, the control device 28 determines an estimated pulse pressure EPM corresponding to each of the pulse period values $T_n$ determined at SB5. More specifically described, the control device 28 selects one of the curves $f_m$ shown in FIG. 5, based on the last pulse period $T_{n-1}$ preceding the each pulse period $T_n$, and determines an estimated pulse pressure EPM according to the thus selected curve $f_m$ based on the each pulse period $T_n$.

Subsequently, the control goes to Steps SB7 and SB8 corresponding to the estimated-blood-pressure determining means 71. First, at SB7, the control device 28 determines, according to the predetermined relationship between estimated diastolic blood pressure $EBP_{DIA}$ and heart period T, shown in FIG. 6, an estimated diastolic blood pressure $EBP_{DIA}$ based on each of the pulse period values $T_n$ determined at SB5. Then, at SB8, the control device 28 adds half the estimated pulse pressure $EPM_n$ determined at SB6 for the each pulse period $T_n$, i.e., the additional pressure α, to the estimated diastolic blood pressure $EBP_{DIA}$ determined at SB7 for the each pulse period $T_n$, so as to determine an estimated middle blood pressure $EBP_{MID(n)}$ for the each pulse period $T_n$.

Then, the control goes to Steps SB9 and SB10 corresponding to the blood-pressure-correction-value determining means 72. First, at SB9, the control device 28 determines an average of the respective estimated middle blood pressure values $EBP_{MID(n)}$ determined at SB8 for the respective pulse period values $T_n$, that is, an average estimated middle blood pressure $MID_{PER}$ of the respective estimated middle blood pressure values $EBP_{MID(n)}$ during the slow decreasing of the cuff pressure $P_C$. Then, at SB10, the control device 28 determines, for each of the pulse period values $T_n$, a blood-pressure correction value $\Delta P_n$ by subtracting the average estimated middle blood pressure $MID_{per}$ determined at SB9, from the estimated middle blood pressure $EBP_{MID(n)}$ determined for the each pulse period value $T_n$ at SB8.

Subsequently, at SB11, the control device 28 identifies one of the heartbeat-synchronous pulses of the cuff pulse wave $WK_n$ that corresponds to the blood-pressure correction value $\Delta P_n$ determined for each of the pulse period values $T_n$ at SB10, that is, corresponds to the first one of the two successive pulses $WH_n$, $WH_{n+1}$ of the ECG wave that have been used to determine the each pulse period value $T_n$.

Then, at SB12, the control device 28 determines a value $PRS_n$ of the cuff pressure $P_C$ at the time of detection of the amplitude $AK_n$ of the one pulse $WK_n$ of the cuff pulse wave that has been identified at SB11 as corresponding to the blood-pressure correction value $\Delta P_n$ for each of the pulse period values $T_n$. Then, at SB13 corresponding to the corrected-cuff-pressure determining means 74, the control device 28 subtracts, from the cuff pressure $PRS_n$ determined at SB12, the blood-pressure correction value $\Delta P_n$ determined at SB10 and corresponding to the cuff pressure $PRS_n$, and thereby determines a corrected cuff pressure $PRS_n'$.

Then, at SB14 corresponding to the blood-pressure determining means 76, the control device 28 determines a systolic blood-pressure value $BP_{SYS}$, a mean blood-pressure value $BP_{MEAN}$, and a diastolic blood-pressure value $BP_{DIA}$ of the patient, based on the change of the respective corrected cuff-pulse-wave amplitudes $AK_n'$ determined at SB4, with respect to the respective corrected cuff-pressure values $PRS_n'$ determined at SB13, according to a well-known oscillometric algorithm. Then, at SB15, the systolic blood-pressure value $BP_{SYS}$, etc. determined at SB10 are displayed on the display device 36. Thus, the present routine is finished.

It emerges from the foregoing description of the illustrated embodiment, that the correction-factor determining means 64 (SB3) determines, for each of the pulses $WL_n$ of the photoelectric pulse wave continuously detected by the photoelectric-pulse-wave sensor 40, the correction factor $K_n$ to correct the amplitude $AL_n$ of the each pulse $WL_n$ to the average amplitude $AL_{per}$; and the corrected-cuff-pulse-wave-amplitude determining means 66 (SB4) multiplies, by the correction factor $K_n$ determined for the each pulse $WL_n$, the amplitude $AK_n$ of one of the pulses $WK_n$ of the cuff pulse wave that corresponds to the each pulse $WL_n$, and thereby determines the corrected amplitude $AK_n'$ of the one pulse $WK_n$ that is free of the influence of change of cardiac output during the slow changing of the cuff pressure $P_C$.

In addition, in the illustrated embodiment, the estimated-blood-pressure determining means 71 (SB7 and SB8) determines the estimated middle blood pressure $EBP_{MID(n)}$ based on each pulse period $T_n$; and the blood-pressure-correction-value determining means 72 (SB9 and SB10) determines, for each pulse period $T_n$, the blood-pressure correction value $\Delta P_n$ to correct the estimated middle blood pressure $EBP_{MID(n)}$ to the average estimated middle blood pressure $MID_{PE}R$. The corrected-cuff-pressure determining means 74 (SB13) subtracts, from the cuff pressure $PRS_n$ at the time of detection of the amplitude $AK_n$ of one of the pulses $WK_n$ of the cuff pulse wave that corresponds to each pulse period $T_n$, the blood-pressure correction value $\Delta P_n$ determine for the each pulse period $T_n$, and thereby determines the corrected cuff pressure $PRS_n'$ that indicates a cuff pressure $P_C$ which would be detected, at the time of detection of the amplitude $AK_n$ of the one pulse $WK_n$ of the cuff pulse wave, in the state in which there would be no influence of change of blood pressure of the subject. And, the blood-pressure determining means 76 (SB14) determines the blood pressure BP of the subject based on the change of the respective corrected cuff-pulse-wave amplitudes $AK_n'$ determined by the corrected-cuff-pulse-wave-amplitude determining means 66 (SB4) with respect to the respective corrected cuff-pressure values $PRS_n'$ determined by the corrected-cuff-pressure determining means 74 (SB13). Thus, the present apparatus 8 can determine the blood pressure BP with high accuracy.

Next, there will be described a second embodiment of the present invention. The same reference numerals as used in the preceding embodiment are used to designate the corresponding elements of the second embodiment and the description thereof is omitted.

Figure 9:
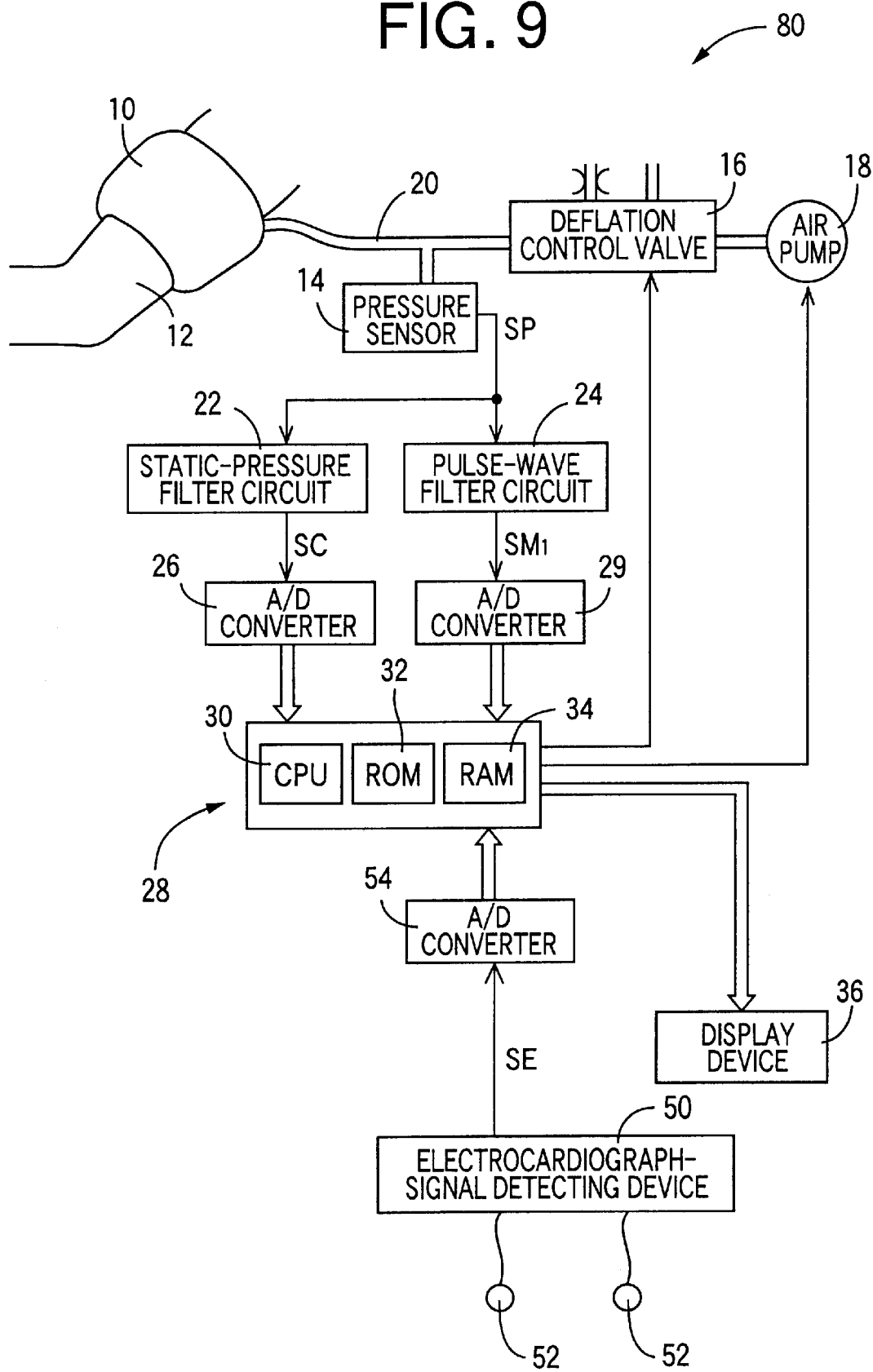
FIG. 9 is a diagrammatic view for explaining a construction of another automatic blood-pressure measuring apparatus as another embodiment of the present invention.

The second embodiment relates to an automatic blood-pressure measuring apparatus 80 whose construction is shown in the diagrammatic view of FIG. 9. This automatic blood-pressure measuring apparatus 80 differs from the automatic blood-pressure measuring apparatus 8, in that the former apparatus 80 does not include the photoelectric-pulse-wave sensor 40 or the A/D converter 48 and in that the control device 28 of the former apparatus 80 is operated in a different manner from that in which the control device 28 of the latter apparatus 8 shown in FIG. 2 is operated.

Figure 10:
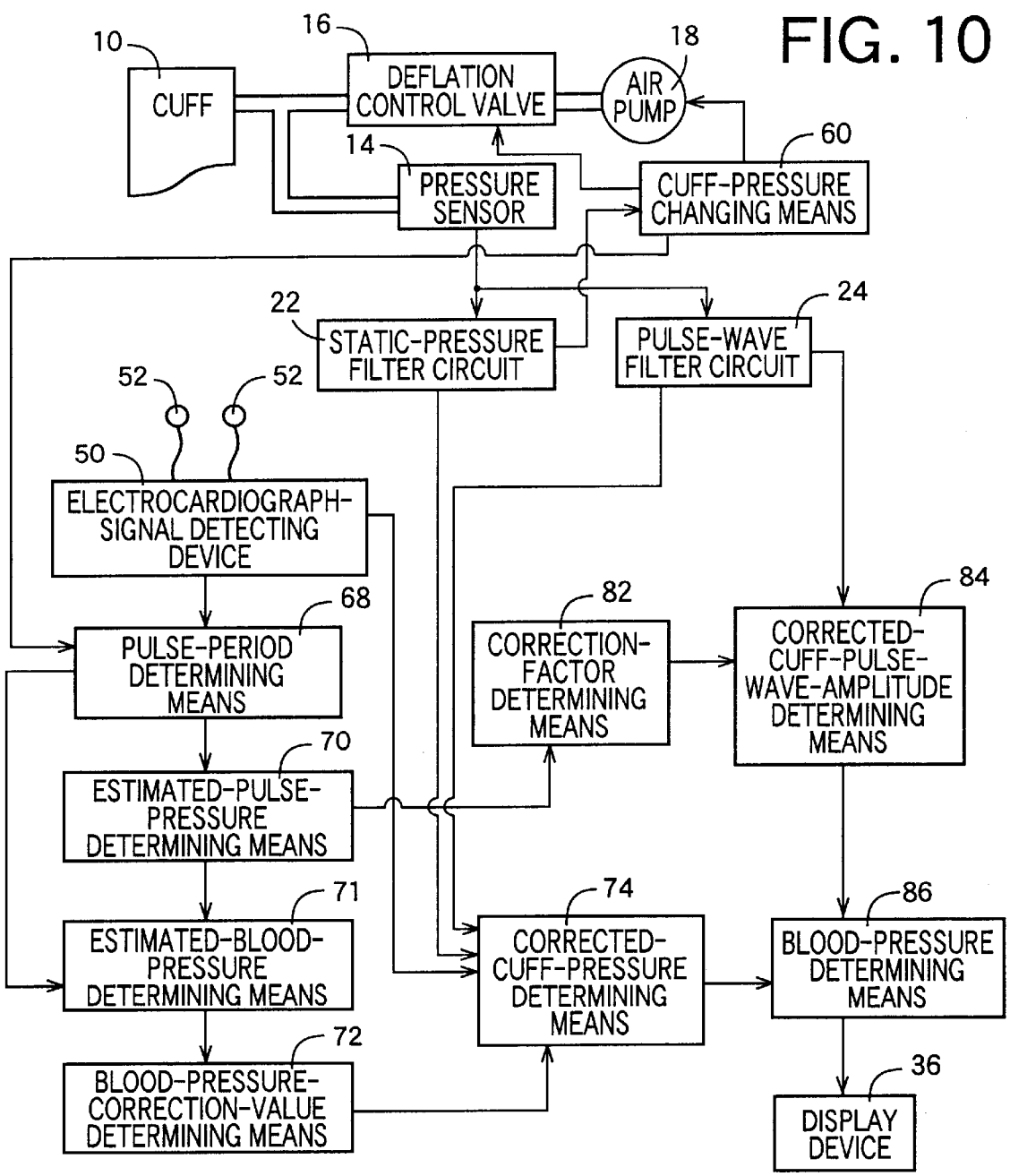
FIG. 10 is a block diagram for explaining essential functions of a control device of the automatic blood-pressure measuring apparatus of FIG. 9.

FIG. 10 is a block diagram for explaining essential functions of the control device 28 of the automatic blood-pressure measuring apparatus 80. In the figure, a correction-factor determining means 82 determines a correction factor $C_n$ to correct each of the respective estimated pulse pressure values $EPM_n$ determined by the estimated-pulse-pressure determining means 70 for the respective pulse period values $T_n$, to a predetermined value, for example, an average estimated pulse pressure $EPM_{PER}$ of the respective estimated pulse pressure values $EPM_n$ obtained during the blood-pressure measuring operation, according to the following expression (6):

$$C_n = EPM_{per}/EPM_n \tag{6}$$

Each correction factor $C_n$ is obtained by dividing the average estimated pulse pressure $EPM_{PER}$ by each of the estimated pulse pressure values $EPM_n$.

A corrected-cuff-pulse-wave-amplitude determining means 84 multiplies, by the correction factor $C_n$ determined for each of the estimated pulse pressure values $EPM_n$ by the correction-factor determining means 82, an amplitude $AK_n$ of one of the heartbeat-synchronous pulses $WK_n$ of the cuff pulse wave that corresponds to the each estimated pulse pressure value $EPM_n$, and thereby determines a corrected amplitude $AK_n'$ of the one pulse $WK_n$ of the cuff pulse wave, according to the following expression (7):

$$AK_n' = AK_n \times C_n \tag{7}$$

The each estimated pulse pressure $EPM_n$ and the corresponding one pulse $WK_n$ of the cuff pulse wave are produced by a same heartbeat of the patient.

The correction factor $C_n$ determined by the correction-factor determining means 82 is a factor for correcting the estimated pulse pressure $EPM_n$ to a predetermined value. That is, the correction factors $C_n$ are factors for removing respective fluctuations of the respective estimated pulse pressure values $EPM_n$ obtained during the slow decreasing of the cuff pressure $P_C$. Therefore, the respective corrected cuff-pulse-wave amplitudes $AK_n'$ obtained by multiplying the respective amplitudes $AK_n$ of the pulses $WK_n$ by the corresponding correction factors $C_n$, are free of the fluctuations of the cardiac output of the patient during the slow decreasing of the cuff pressure $P_C$.

A blood-pressure determining means 86 determines a systolic blood-pressure value $BP_{SYS}$, a mean blood-pressure value $BP_{MEAN}$, and a diastolic blood-pressure value $BP_{DIA}$ of the patient, based on the change of the respective corrected cuff-pulse-wave amplitudes $AK_n'$ determined by the corrected-cuff-pulse-wave-amplitude determining means 84, with respect to the respective corrected cuff-pressure values $PRS_n'$ determined by the corrected-cuff-pressure determining means 74, according to an oscillometric blood-pressure determining algorithm.

Figure 11:
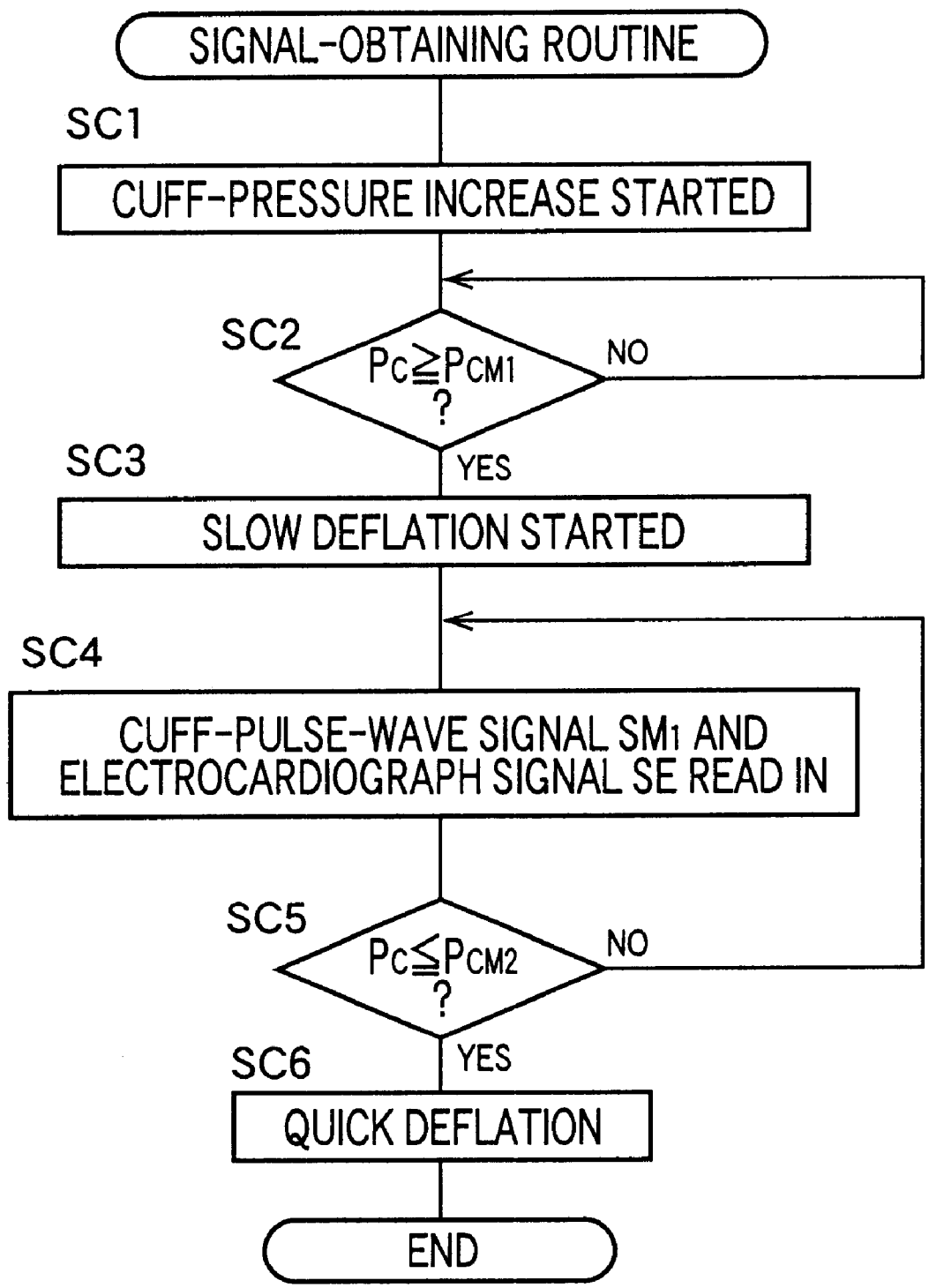
FIG. 11 is a flow chart representing a signal-obtaining routine according to which the control device of FIG. 9 obtains signals to determine a blood pressure BP.
Figure 12:
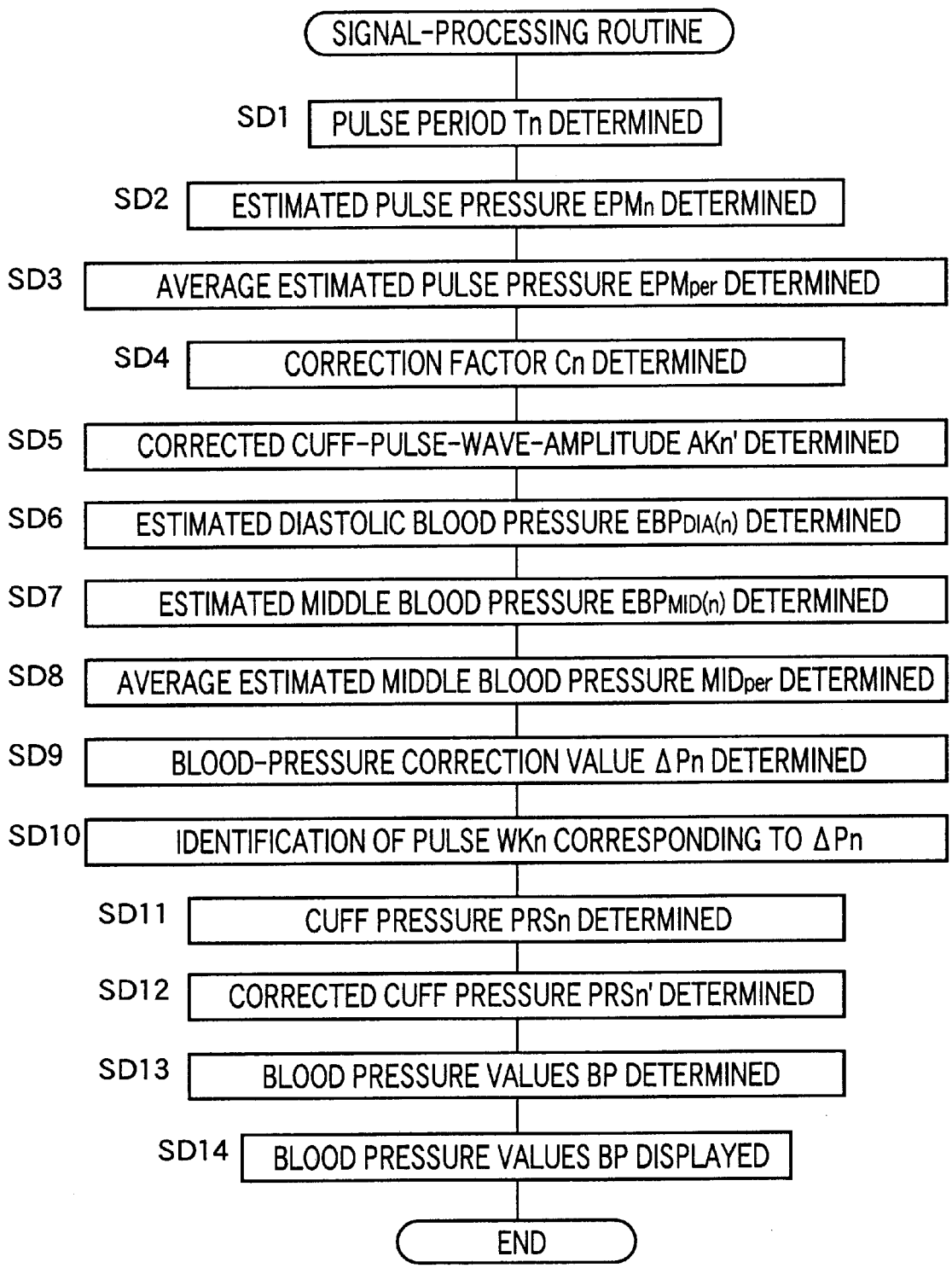
FIG. 12 is a flow chart representing a signal-processing routine according to which the control device of FIG. 9 processes the signals obtained according to the signal-obtaining routine of FIG. 11 and thereby determines the blood pressure.

FIGS. 11 and 12 are flow charts representing essential functions of the control device 28 shown in FIG. 10. FIG. 11 shows a signal-obtaining routine for obtaining signals to determine a blood pressure BP of the patient; and FIG. 12 shows a signal-processing routine for processing the signals obtained according to the signal-obtaining routine of FIG. 11 and thereby determining the blood pressure BP.

In the signal-obtaining routine of FIG. 11, Steps SC1, SC2, SC3, SC5, and SC6 are the same steps as Steps SA1, SA2, SA3, SA5, and SA6 of FIG. 7, respectively.

Step SC4 shown in FIG. 11 differs from Step SA4 shown in FIG. 7, in that at SC4 the control device 28 does not read in the photoelectric-pulse-wave signal $SM_2$ supplied from the photoelectric-pulse-wave sensor 40. That is, at SC4, the control device 28 reads in the cuff-pressure-pulse signal $SM_1$ supplied from the pulse-wave filter circuit 24, and the ECG signal SE supplied from the ECG-signal detecting device 50, each during the slow decreasing of the cuff pressure $P_C$.

The signal-obtaining routine of FIG. 11 is followed by the signal-processing routine of FIG. 12. First, at SD1 corresponding to the pulse-period determining means 68, the control device 28 identifies an R-wave of each of the heartbeat-synchronous pulses $WH_n$ of the ECG wave that have been read while Steps SA4 and SA5 of FIG. 11 are repeated and the cuff pressure $P_C$ is slowly decreased, and additionally determines, based on respective distances among the thus determined R-waves, successive pulse period values $T_n$ during the blood pressure measuring operation.

Then, at SD2 corresponding to the estimated-pulse-pressure determining means 70, the control device 28 determines, like at SB6 of FIG. 8, an estimated pulse pressure EPM corresponding to each of the pulse period values $T_n$ determined at SD1, based on the each pulse period value $T_n$. Subsequently, at SD3, the control device 28 determines an average estimated pulse pressure $EPM_{PER}$ of the respective estimated estimated pulse pressure values $EPM_n$ determined at SD2 for the respective pulse period values $T_n$.

Then, at SD4 corresponding to the correction-factor determining means 82, the control device 28 determines a correction factor $C_n$ for each estimated pulse pressure $EPM_n$, by dividing the average estimated pulse pressure $EPM_{per}$ determined at SD3, by each of the estimated pulse pressure values $EPM_n$ determined at SD2, according to the previously-indicated expression (6).

Then, at SD5 corresponding to the corrected-cuff-pulse-wave-amplitude determining means 84, the control device 28 multiplies, by the correction factor $C_n$ determined for each estimated pulse pressure $EPM_n$ at SD4, the amplitude $AK_n$ of one of the pulses $WK_n$ of the cuff pulse wave that corresponds to the each estimated pulse pressure $EPM_n$, and thereby determines a corrected amplitude $AK_n'$ of the one pulse $WK_n$.

Steps SD6 through SD14 of FIG. 12 are the same steps as Steps SB7 through SB15 of FIG. 8. Thus, the control device 28 determines, at SD13, blood pressure values BP of the patient and displays, at SD14, the thus determined blood pressure values BP on the display device 36.

As is apparent from the foregoing description of the second embodiment, the correction-factor determining means 82 (SD4) determines, for each of the respective estimated pulse pressure values $EPM_n$ determined by the estimated-pulse-pressure determining means 71 (SD2) for the respective pulse period values $T_n$, the correction factor $K_n$ to correct the each estimated pulse pressure value $EPM_n$ to the average estimated pulse pressure $EPM_{per}$; and the corrected-cuff-pulse-wave-amplitude determining means 84 (SD5) multiplies, by the correction factor $K_n$ determined for the each estimated pulse pressure $EPM_n$, the amplitude $AK_n$ of one of the pulses $WK_n$ of the cuff pulse wave that corresponds to the each estimated pulse pressure $EPM_n$, and thereby determines the corrected amplitude $AK_n'$ of the one pulse $WK_n$ that is free of the influence of change of cardiac output during the slow changing of the cuff pressure $P_C$. In addition, the pulse-period determining means 68 (SD1) determines the pulse period $T_n$ of each of the heartbeat-synchronous pulses $WH_n$ of the ECG wave continuously detected by the ECG-signal detecting device 50; and the blood-pressure-correction-value determining means 72 (SD8 and SD9) determines, for each of the pulse period values $T_n$, the blood-pressure correction value $\Delta P_n$ to correct the estimated blood pressure $EBP_n$, determined based on the each pulse period value $T_n$, to a predetermined value. The corrected-cuff-pressure determining means 74 (SD12) subtracts, from the cuff pressure $PRS_n$ at the time of detection of the amplitude $AK_n$ of one of the pulses $WK_n$ of the cuff pulse wave that corresponds to the each pulse period $T_n$, the blood-pressure correction value $\Delta P_n$ determine for the each pulse period $T_n$, and thereby determines the corrected cuff pressure $PRS_n'$ that indicates a cuff pressure $P_C$ which would be detected, at the time of detection of the amplitude $AK_n$ of the one pulse $WK_n$ of the cuff pulse wave, in the state in which there would be no influence of change of blood pressure of the subject. And, the blood-pressure determining means 86 (SD13) determines the blood pressure BP of the subject based on the change of the respective corrected cuff-pulse-wave amplitudes $AK_n'$ determined by the corrected-cuff-pulse-wave-amplitude determining means 84 (SD5) with respect to the respective corrected cuff-pressure values $PRS_n'$ determined by the corrected-cuff-pressure determining means 74 (SD12). Thus, the present apparatus 80 can determine the blood pressure BP with high accuracy.

While the present invention has been described in its preferred embodiments by reference to the drawings, it is to be understood that the invention may otherwise be embodied.

For example, in the first embodiment, the average-amplitude determining means 62 determines the average amplitude $AL_{per}$ of the respective amplitudes $AL_n$ of the respective pulses $WL_n$ of the photoelectric pulse wave detected during the slow changing of the cuff pressure $P_C$; and the correction-factor determining means 64 determines, by dividing the average amplitude $AL_{per}$ by the amplitude $AL_n$ of each of the pulses $WL_n$ according to the expression (1), the correction factor $K_n$ to correct the amplitude $AL_n$ of the each pulse $WL_n$ to the average amplitude $AL_{per}$ (i.e., a predetermined value). However, the correction factors $K_n$ may be any values that correct the respective amplitudes $AL_n$ of the pulses $WL_n$ each to a predetermined value. Therefore, in the expression (1), the average amplitude $AL_{per}$ may be replaced with, e.g., a prescribed standard value, or an amplitude $AL_n$ of a first pulse $WL_1$ of the photoelectric pulse wave that is first detected by the photoelectric-pulse-wave sensor 40 during the slow decreasing of the cuff pressure $P_C$.

In each of the illustrated embodiments, the cuff-pressure changing means 60 (SA3 and SA5) slowly decreases the cuff pressure $P_C$ down to the prescribed second target pressure $P_{CM2}$. However, the average-amplitude determining means 62 (SB1 and SB2), the correction-factor determining means 64 (SB3), the corrected-cuff-pulse-wave-amplitude determining means 66 (SB4), the pulse-period determining means 68 (SB5), the average-pulse-period determining means 70 (SB6), the blood-pressure-correction-value determining means 72 (SB7, SB8, SB9), the corrected-cuff-pressure determining means 74 (SB12), and the blood-pressure determining means 76 (SB13) may be modified such that during the slow decreasing of the cuff pressure $P_C$, those means 62, 64, 66, 68, 70, 72, 74, 76 iteratively operate at respective times to process respective lengths of the cuff-pulse-wave signal $SM_1$ and the photoelectric-pulse-wave signal $SM_2$ that have been read up to each of those times. In the latter case, the slow decreasing of the cuff pressure $P_C$ may be stopped upon determination of the diastolic blood pressure $BP_{DIA}$.

In each of the illustrated embodiments, both the cuff-pressure values $PRS_n$ and the cuff-pulse-wave amplitudes $AK_n$ are corrected to the corrected cuff-pressure values $PRS_n'$ and the cuff-pulse-wave amplitudes $AK_n'$, respectively, based on which the blood pressure BP is determined. However, it is possible to correct either the cuff-pressure values $PRS_n$ or the cuff-pulse-wave amplitudes $AK_n$ to the corrected cuff-pressure values $PRS_n'$ or the corrected cuff-pulse-wave amplitudes $AK_n'$, because a blood pressure BP determined based on the cuff-pressure values $PRS_n$ or the cuff-pulse-wave amplitudes $AK_n$, and the corrected cuff-pulse-wave amplitudes $AK_n'$ or the corrected cuff-pressure values $PRS_n'$ is freed, to some degree, of the influence of change of blood pressure of the subject during the blood-pressure measuring operation.

In each of the illustrated embodiments, the ECG-signal detecting device 50 is employed as the heartbeat-synchronous wave detecting device. However, the photoelectric-pulse-wave sensor 40 may be used as the heartbeat-synchronous wave detecting device, because the photoelectric pulse wave detected by the sensor 40 is a sort of heartbeat-synchronous wave. In the latter case, the sensor 40 functions as both the volumetric-pulse-wave detecting device and the synchronous-pulse-wave detecting device, and accordingly the automatic blood-pressure measuring apparatus 8, 80 can be produced at lower cost.

In each of the illustrated embodiments, the photoelectric-pulse-wave sensor 40 is employed as the volumetric-pulse-wave detecting device. The sensor 40 is of a transmission type that detects the change of amount of blood based on the amount of light transmitted through the portion of the patient. However, the sensor 40 may be replaced with a photoelectric-pulse-wave sensor of a reflection type that detects the change of amount of blood based on the amount of light reflected from a portion of a living subject; an impedance-pulse-wave that detects the change of amount of blood based on the change of impedance between prescribed portions of a living subject; or a volume-change detecting device that covers a portion of a living subject, such as an end portion of a finger, and detects the change of amount of blood based on the change of volume of the portion of the subject.

It is to be understood that the present invention may be embodied with other changes, improvements, and modifications that may occur to a person skilled in the art without departing from the spirit and scope of the invention defined in the appended claims.

What is claimed is:

1. An apparatus for automatically measuring a blood pressure of a living subject, comprising:

an inflatable cuff which is adapted to be wound around a portion of the subject, where a cuff pulse wave including a plurality of heartbeat-synchronous pulses occurs to the cuff when a pressure in the cuff is changed;

a heartbeat-synchronous-wave detecting device which detects, from the subject, a heartbeat-synchronous wave including a plurality of heartbeat-synchronous pulses;

a pulse-period determining means for iteratively determining a pulse period of the subject based on a time interval between respective prescribed periodic points of each pair of successive heartbeat-synchronous pulses of the heartbeat-synchronous wave detected by the heartbeat-synchronous-wave detecting device during the changing of the pressure of the cuff;

an estimated-pulse-pressure determining means for iteratively determining, for each of the pulse periods iteratively determined by the pulse-period determining means, an estimated pulse pressure of the subject during the changing of the pressure of the cuff, based on each pair of successive pulse periods of the pulse periods, according to a predetermined relationship between pulse pressure and a pair of successive pulse periods;

a correction-factor determining means for iteratively determining, for each of the estimated pulse pressures iteratively determined by the estimated pulse pressure determining means, a correction factor to correct said each estimated pulse pressure, to a predetermined value;

a corrected-cuff-pulse-wave-amplitude determining means for iteratively multiplying, by the correction factor determined by the correction-factor determining means for said each of the estimated pulse pressures, an amplitude of one of the heartbeat-synchronous pulses of the cuff pulse wave that corresponds to said each of the estimated pulse pressures, and thereby iteratively determining a corrected amplitude of said one heartbeat-synchronous pulse of the cuff pulse wave;

an estimated-blood-pressure determining means for iteratively determining an estimated blood pressure of the subject during the changing of the pressure of the cuff, based on said each of the pulse periods iteratively determined by the pulse-period determining means, according to a predetermined relationship between estimated blood pressure and pulse period;

a blood-pressure-correction-value determining means for iteratively determining, for said each of the pulse periods, a blood-pressure correction value to correct a corresponding one of the estimated blood pressures iteratively determined by the estimated-blood-pressure determining means, to a predetermined value;

a corrected-cuff-pressure determining means for subtracting, from a pressure of the cuff at a time of detection of one of the heartbeat-synchronous pulses of the cuff pulse wave that corresponds to said each of the pulse periods, the blood-pressure correction value determined by the blood-pressure-correction-value determining means for said each of the pulse periods, and thereby determining a corrected pressure of the cuff for said each of the pulse periods; and a blood-pressure determining means for determining a blood pressure of the subject based on a change of the respective corrected amplitudes of the respective heartbeat-synchronous pulses of the cuff pulse wave determined by the corrected-cuff-pulse-wave-amplitude determining means, with respect to the respective corrected pressures of the cuff determined by the corrected-cuff-pressure determining means for the respective pulse periods.

2. An apparatus according to claim 1, further comprising:

a pressure changing device which changes the pressure of the cuff;

a pressure sensor which detects the pressure of the cuff changed by the pressure changing device; and a cuff-pulse-wave detecting device which detects the cuff pulse wave occurring to the cuff when the pressure of the cuff is changed by the pressure changing device.

3. An apparatus for automatically measuring a blood pressure of a living subject, comprising:

an inflatable cuff which is adapted to be wound around a first portion of the subject, where a cuff pulse wave including a plurality of heartbeat-synchronous pulses occurs to the cuff when a pressure in the cuff is changed;

a volumetric-pulse-wave detecting device which is adapted to be worn on a second portion of the subject and which detects, from the second portion of the subject, a volumetric pulse wave including a plurality of heartbeat-synchronous pulses;

a correction-factor determining means for iteratively determining, for each of the heartbeat-synchronous pulses of the volumetric pulse wave, a correction factor to correct an amplitude of said each heartbeat-synchronous pulse to a predetermined value;

a corrected-cuff-pulse-wave-amplitude determining means for iteratively multiplying, by the correction factor determined by the correction-factor determining means for said each of the heartbeat-synchronous pulses of the volumetric pulse wave, an amplitude of one of the heartbeat-synchronous pulses of the cuff pulse wave that corresponds to said each heartbeat-synchronous pulse of the volumetric pulse wave, and thereby determining a corrected amplitude of said one heartbeat-synchronous pulse of the cuff pulse wave;

a heartbeat-synchronous-wave detecting device which detects, from the subject, a heartbeat-synchronous wave including a plurality of heartbeat-synchronous pulses;

a pulse-period determining means for iteratively determining a pulse period of the subject based on a time interval between respective prescribed periodic points of each pair of successive heartbeat-synchronous pulses of the heartbeat-synchronous wave detected by the heartbeat-synchronous-wave detecting device during the changing of the pressure of the cuff;

an estimated-blood-pressure determining means for iteratively determining an estimated blood pressure of the subject during the changing of the pressure of the cuff, based on each of the pulse periods iteratively determined by the pulse-period determining means, according to a predetermined relationship between estimated blood pressure and pulse period;

a blood-pressure-correction-value determining means for iteratively determining, for said each of the pulse periods, a blood-pressure correction value to correct a corresponding one of the estimated blood pressures iteratively determined by the estimated-blood-pressure determining means, to a predetermined value;

a corrected-cuff-pressure determining means for subtracting, from a pressure of the cuff at a time of detection of one of the heartbeat-synchronous pulses of the cuff pulse wave that corresponds to said each of the pulse periods, the blood-pressure correction value determined by the blood-pressure-correction-value determining means for said each of the pulse periods, and thereby determining a corrected pressure of the cuff for said each of the pulse periods; and a blood-pressure determining means for determining a blood pressure of the subject based on a change of the respective corrected amplitudes of the respective heartbeat-synchronous pulses of the cuff pulse wave determined by the corrected-cuff-pulse-wave-amplitude determining means, with respect to the respective corrected pressures of the cuff determined by the corrected-cuff-pressure determining means for the respective pulse periods.

4. An apparatus for automatically measuring a blood pressure of a living subject, comprising:

an inflatable cuff which is adapted to be wound around a portion of the subject, where a cuff pulse wave including a plurality of heartbeat-synchronous pulses occurs to the cuff when a pressure in the cuff is changed;

a heartbeat-synchronous-wave detecting device which detects, from the subject, a heartbeat-synchronous wave including a plurality of heartbeat-synchronous pulses;

a pulse-period determining means for iteratively determining a pulse period of the subject based on a time interval between respective prescribed periodic points of each pair of successive heartbeat-synchronous pulses of the heartbeat-synchronous wave detected by the heartbeat-synchronous-wave detecting device during the changing of the pressure of the cuff;

an estimated-pulse-pressure determining means for iteratively determining, for each of the pulse periods iteratively determined by the pulse-period determining means, an estimated pulse pressure of the subject during the changing of the pressure of the cuff, based on each pair of successive pulse periods of the pulse periods, according to a predetermined relationship between pulse pressure and a pair of successive pulse periods;

a correction-factor determining means for iteratively determining, for each of the estimated pulse pressures iteratively determined by the estimated pulse pressure determining means, a correction factor to correct said each estimated pulse pressure to a predetermined value;

a corrected-cuff-pulse-wave-amplitude determining means for iteratively multiplying, by the correction factor determined by the correction-factor determining means for said each of the estimated pulse pressures, an amplitude of one of the heartbeat-synchronous pulses of the cuff pulse wave that corresponds to said each of the estimated pulse pressures, and thereby iteratively determining a corrected amplitude of said one heartbeat-synchronous pulse of the cuff pulse wave; and a blood-pressure determining means for determining a blood pressure of the subject based on a change of the respective corrected amplitudes of the respective heartbeat-synchronous pulses of the cuff pulse wave, with respect to the pressure of the cuff.

5. An apparatus according to claim 4, wherein the correction-factor determining means comprises:

means for determining, as the predetermined value, an average estimated pulse pressure of the respective estimated pulse pressures iteratively determined by the estimated-pulse-pressure determining means; and means for iteratively determining, for said each of the estimated pulse pressures, the correction factor to correct said each estimated pulse pressure to the determined average estimated pulse pressure.

6. An apparatus for automatically measuring a blood pressure of a living subject, comprising:

an inflatable cuff which is adapted to be wound around a first portion of the subject, where a cuff pulse wave including a plurality of heartbeat-synchronous pulses occurs to the cuff when a pressure in the cuff is changed;

a volumetric-pulse-wave detecting device which is adapted to be worn on a second portion of the subject and which detects, from the second portion of the subject, a volumetric pulse wave including a plurality of heartbeat-synchronous pulses;

a correction-factor determining means for iteratively determining, for each of the heartbeat-synchronous pulses of the volumetric pulse wave, a correction factor to correct an amplitude of said each heartbeat-synchronous pulse to a predetermined value;

a corrected-cuff-pulse-wave-amplitude determining means for iteratively multiplying, by the correction factor determined by the correction-factor determining means for said each of the heartbeat-synchronous pulses of the volumetric pulse wave, an amplitude of one of the heartbeat-synchronous pulses of the cuff pulse wave that corresponds to said each heartbeat-synchronous pulse of the volumetric pulse wave, and thereby determining a corrected amplitude of said one heartbeat-synchronous pulse of the cuff pulse wave; and a blood-pressure determining means for determining a blood pressure of the subject based on a change of the respective corrected amplitudes of the respective heartbeat-synchronous pulses of the cuff pulse wave, with respect to the pressure of the cuff.

7. An apparatus according to claim 1, wherein the volumetric-pulse-wave detecting device comprises a photoelectric-pulse-wave detecting device including a light emitter emitting a light toward the second portion of the subject and a light receiver receiving the light from the second portion.

8. An apparatus according to claim 1, wherein the correction-factor determining means comprises:

means for determining an average amplitude of respective amplitudes of the heartbeat-synchronous pulses of the volumetric pulse wave; and means for determining, for said each of the heartbeat-synchronous pulses of the volumetric pulse wave, the correction factor to correct the amplitude of said each heartbeat-synchronous pulse to the determined average amplitude as the predetermined value.

9. An apparatus for automatically measuring a blood pressure of a living subject, comprising:

an inflatable cuff which is adapted to be wound around a portion of the subject, where a cuff pulse wave including a plurality of heartbeat-synchronous pulses occurs to the cuff when a pressure in the cuff is changed;

a heartbeat-synchronous-wave detecting device which detects, from the subject, a heartbeat-synchronous wave including a plurality of heartbeat-synchronous pulses;

a pulse-period determining means for iteratively determining a pulse period of the subject based on a time interval between respective prescribed periodic points of each pair of successive heartbeat-synchronous pulses of the heartbeat-synchronous wave detected by the heartbeat-synchronous-wave detecting device during the changing of the pressure of the cuff;

an estimated-blood-pressure determining means for iteratively determining an estimated blood pressure of the subject during the changing of the pressure of the cuff, based on each of the pulse periods iteratively determined by the pulse-period determining means, according to a predetermined relationship between estimated blood pressure and pulse period;

a blood-pressure-correction-value determining means for iteratively determining, for said each of the pulse periods, a blood-pressure correction value to correct a corresponding one of the estimated blood pressures iteratively determined by the estimated-blood-pressure determining means, to a predetermined value;

a corrected-cuff-pressure determining means for subtracting, from a pressure of the cuff at a time of detection of one of the heartbeat-synchronous pulses of the cuff pulse wave that corresponds to said each of the pulse periods, the blood-pressure correction value determined by the blood-pressure-correction-value determining means for said each of the pulse periods, and thereby determining a corrected pressure of the cuff for said each of the pulse periods; and a blood-pressure determining means for determining a blood pressure of the subject based on a change of respective amplitudes of the respective heartbeat-synchronous pulses of the cuff pulse wave, with respect to the respective corrected pressures of the cuff determined by the corrected-cuff-pressure determining means for the respective pulse periods.

10. An apparatus according to claim 9, wherein the blood-pressure-correction-value determining means comprises means for determining, as the predetermined value, an average estimated blood pressure of the respective estimated blood pressures iteratively determined by the estimated-blood-pressure determining means, and means for iteratively determining, for said each of the pulse periods, the blood-pressure correction value to correct said corresponding one of the estimated blood pressures iteratively determined by the estimated-blood-pressure determining means, to the average estimated blood pressure, and wherein the corrected-cuff-pressure determining means comprises means for subtracting, from the pressure of the cuff at the time of detection of said one of the heartbeat-synchronous pulses of the cuff pulse wave that corresponds to said each of the pulse periods, the blood pressure correction value determined for said each of the pulse periods, and thereby determining the corrected pressure of the cuff.

11. An apparatus according to claim 9, wherein the heartbeat-synchronous-wave detecting device comprises an electrocardiograph-wave detecting device which detects, as the heartbeat-synchronous wave, an electrocardiograph wave including a plurality of heartbeat-synchronous pulses.

* * * * *